(12) United States Patent
Morris et al.

(10) Patent No.: US 8,192,401 B2
(45) Date of Patent: Jun. 5, 2012

(54) MEDICAL FLUID PUMP SYSTEMS AND RELATED COMPONENTS AND METHODS

(75) Inventors: Jules Jay Morris, Chestnut Hill, MA (US); Thomas Irvin Folden, Alamo, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 294 days.

(21) Appl. No.: 12/725,673

(22) Filed: Mar. 17, 2010

(65) Prior Publication Data

US 2010/0241062 A1 Sep. 23, 2010

Related U.S. Application Data

(60) Provisional application No. 61/162,134, filed on Mar. 20, 2009.

(51) Int. Cl.
*A61M 1/00* (2006.01)
(52) U.S. Cl. ...................................................... 604/153
(58) Field of Classification Search ............... 417/477.2; 604/27, 29, 131, 132, 140, 141, 146, 151–153
See application file for complete search history.

(56) References Cited

U.S. PATENT DOCUMENTS

| | | |
|---|---|---|
| 3,927,955 A | 12/1975 | Spinosa et al. |
| 3,985,135 A | 10/1976 | Carpenter et al. |
| 4,026,669 A | 5/1977 | Leonard et al. |
| 4,303,376 A | 12/1981 | Siekmann |
| 4,370,983 A | 2/1983 | Lichtenstein |
| 4,382,753 A | 5/1983 | Archibald |
| 4,436,620 A | 3/1984 | Bellotti et al. |
| 4,453,932 A | 6/1984 | Pastrone |
| 4,479,762 A | 10/1984 | Bilstad et al. |
| 4,623,328 A | 11/1986 | Hartranft |
| 4,628,499 A | 12/1986 | Hammett |
| 4,643,713 A | 2/1987 | Viitala |
| 4,657,490 A | 4/1987 | Abbott |
| 4,662,906 A | 5/1987 | Matkovich et al. |
| 4,676,467 A | 6/1987 | Palsulich |
| 4,710,166 A | 12/1987 | Thompson et al. |
| 4,778,451 A | 10/1988 | Kamen |
| 4,808,161 A | 2/1989 | Kamen |
| 4,826,482 A | 5/1989 | Kamen |
| 4,840,542 A | 6/1989 | Abbott |
| 4,902,282 A | 2/1990 | Bellotti et al. |
| 4,927,411 A | 5/1990 | Pastrone et al. |
| 4,950,134 A | 8/1990 | Bailey et al. |

(Continued)

FOREIGN PATENT DOCUMENTS

DE 198 37 667 3/2000

(Continued)

OTHER PUBLICATIONS

Liberty Cycler Operator's Manual, 2003-2004.

(Continued)

*Primary Examiner* — Bhisma Mehta
*Assistant Examiner* — Bradley Osinski
(74) *Attorney, Agent, or Firm* — Fish & Richardson P.C.

(57) ABSTRACT

A medical fluid delivery cassette configured for use with a medical fluid pumping system. The cassette includes a base, a membrane attached to the base, and an adhesive disposed on a portion of the membrane overlying a fluid pump chamber of the cassette. The portion of the membrane overlying the fluid pump chamber is moveable such that the volume of the fluid pump chamber can be changed.

18 Claims, 17 Drawing Sheets

U.S. PATENT DOCUMENTS

| | | |
|---|---|---|
| 4,976,162 A | 12/1990 | Kamen |
| 4,997,464 A | 3/1991 | Kopf |
| 5,002,471 A | 3/1991 | Perlov |
| 5,036,886 A | 8/1991 | Olsen et al. |
| 5,061,236 A | 10/1991 | Sutherland et al. |
| 5,088,515 A | 2/1992 | Kamen |
| 5,098,262 A | 3/1992 | Wecker et al. |
| 5,100,380 A | 3/1992 | Epstein |
| 5,100,699 A | 3/1992 | Roeser |
| 5,116,021 A | 5/1992 | Faust et al. |
| 5,116,316 A | 5/1992 | Sertic et al. |
| 5,146,713 A | 9/1992 | Grafius |
| 5,151,019 A | 9/1992 | Danby et al. |
| 5,167,837 A | 12/1992 | Snodgrass et al. |
| 5,171,029 A | 12/1992 | Maxwell et al. |
| 5,178,182 A | 1/1993 | Kamen |
| 5,193,990 A | 3/1993 | Kamen et al. |
| 5,211,201 A | 5/1993 | Kamen et al. |
| 5,241,985 A | 9/1993 | Faust et al. |
| 5,247,434 A | 9/1993 | Peterson et al. |
| 5,252,044 A | 10/1993 | Raines et al. |
| 5,279,556 A | 1/1994 | Goi et al. |
| 5,302,093 A | 4/1994 | Owens et al. |
| 5,324,422 A | 6/1994 | Colleran et al. |
| 5,330,425 A | 7/1994 | Utterberg |
| 5,350,357 A | 9/1994 | Kamen et al. |
| D351,470 S | 10/1994 | Scherer et al. |
| 5,353,837 A | 10/1994 | Faust |
| 5,395,351 A | 3/1995 | Munsch |
| 5,421,208 A | 6/1995 | Packard et al. |
| 5,421,823 A | 6/1995 | Kamen et al. |
| 5,427,509 A | 6/1995 | Chapman et al. |
| 5,431,626 A | 7/1995 | Bryant et al. |
| 5,431,627 A | 7/1995 | Pastrone et al. |
| 5,431,634 A | 7/1995 | Brown |
| 5,438,510 A | 8/1995 | Bryant et al. |
| 5,441,636 A | 8/1995 | Chevallet et al. |
| 5,445,506 A | 8/1995 | Afflerbaugh et al. |
| 5,447,286 A | 9/1995 | Kamen et al. |
| 5,462,416 A | 10/1995 | Dennehey et al. |
| 5,462,417 A | 10/1995 | Chapman |
| 5,474,683 A | 12/1995 | Bryant et al. |
| 5,478,211 A | 12/1995 | Dominiak et al. |
| 5,480,294 A | 1/1996 | Di Perna et al. |
| 5,482,438 A | 1/1996 | Anderson et al. |
| 5,482,440 A | 1/1996 | Dennehey et al. |
| 5,482,446 A | 1/1996 | Williamson et al. |
| 5,484,239 A | 1/1996 | Chapman et al. |
| 5,486,286 A | 1/1996 | Peterson et al. |
| 5,514,069 A | 5/1996 | Brown et al. |
| 5,538,405 A | 7/1996 | Patno et al. |
| 5,547,453 A | 8/1996 | Di Perna |
| 5,551,850 A | 9/1996 | Williamson et al. |
| 5,551,941 A | 9/1996 | Howell |
| 5,551,942 A | 9/1996 | Brown et al. |
| 5,554,013 A | 9/1996 | Owens et al. |
| 5,570,716 A | 11/1996 | Kamen et al. |
| 5,578,070 A | 11/1996 | Utterberg |
| 5,609,572 A | 3/1997 | Lang |
| 5,614,677 A | 3/1997 | Wamsiedler et al. |
| 5,628,908 A | 5/1997 | Kamen et al. |
| 5,630,710 A | 5/1997 | Tune et al. |
| 5,634,896 A | 6/1997 | Bryant et al. |
| 5,640,995 A | 6/1997 | Packard et al. |
| 5,641,405 A | 6/1997 | Keshaviah et al. |
| 5,641,892 A | 6/1997 | Larkins et al. |
| 5,643,205 A | 7/1997 | Utterberg |
| 5,658,133 A | 8/1997 | Anderson et al. |
| 5,690,602 A | 11/1997 | Brown et al. |
| D390,654 S | 2/1998 | Alsberg et al. |
| 5,713,865 A | 2/1998 | Manning et al. |
| 5,713,888 A | 2/1998 | Neuenfeldt et al. |
| 5,741,125 A | 4/1998 | Neftel et al. |
| 5,746,708 A | 5/1998 | Giesler et al. |
| 5,755,683 A | 5/1998 | Houle et al. |
| 5,764,034 A | 6/1998 | Bowman et al. |
| 5,771,914 A | 6/1998 | Ling et al. |
| 5,772,635 A | 6/1998 | Dastur et al. |
| 5,772,637 A | 6/1998 | Heinzmann et al. |
| 5,782,805 A | 7/1998 | Meinzer et al. |
| 5,799,207 A | 8/1998 | Wang et al. |
| 5,816,779 A | 10/1998 | Lawless et al. |
| 5,840,151 A | 11/1998 | Munsch |
| 5,842,841 A | 12/1998 | Danby et al. |
| 5,843,035 A | 12/1998 | Bowman et al. |
| 5,868,696 A | 2/1999 | Giesler et al. |
| 5,873,853 A | 2/1999 | Keilman et al. |
| 5,906,598 A | 5/1999 | Giesler et al. |
| 5,935,099 A | 8/1999 | Peterson et al. |
| 5,938,634 A | 8/1999 | Packard |
| 5,989,423 A | 11/1999 | Kamen |
| 5,993,174 A | 11/1999 | Konishi |
| 5,996,634 A | 12/1999 | Dennehey et al. |
| 6,013,057 A | 1/2000 | Danby et al. |
| 6,036,668 A | 3/2000 | Mathis |
| 6,036,680 A | 3/2000 | Horne et al. |
| 6,041,801 A | 3/2000 | Gray et al. |
| 6,065,941 A | 5/2000 | Gray et al. |
| 6,068,612 A | 5/2000 | Bowman et al. |
| 6,074,359 A | 6/2000 | Keshaviah et al. |
| 6,099,492 A | 8/2000 | Le Boeuf |
| 6,118,207 A | 9/2000 | Ormerod et al. |
| 6,129,517 A | 10/2000 | Danby et al. |
| 6,136,565 A | 10/2000 | Best et al. |
| 6,154,605 A | 11/2000 | Aonuma |
| 6,164,621 A | 12/2000 | Bouchard et al. |
| 6,165,154 A | 12/2000 | Gray et al. |
| 6,179,801 B1 | 1/2001 | Holmes et al. |
| 6,184,356 B1 | 2/2001 | Anderson et al. |
| 6,196,987 B1 | 3/2001 | Holmes et al. |
| 6,200,287 B1 | 3/2001 | Keller et al. |
| 6,208,107 B1 | 3/2001 | Maske et al. |
| 6,220,295 B1 | 4/2001 | Bouchard et al. |
| 6,223,130 B1 | 4/2001 | Gray et al. |
| 6,227,807 B1 | 5/2001 | Chase |
| 6,228,047 B1 | 5/2001 | Dadson |
| 6,231,537 B1 | 5/2001 | Holmes et al. |
| 6,234,989 B1 | 5/2001 | Brierton et al. |
| 6,250,502 B1 | 6/2001 | Cote et al. |
| 6,261,065 B1 | 7/2001 | Nayak et al. |
| 6,267,242 B1 | 7/2001 | Nagata et al. |
| 6,270,673 B1 | 8/2001 | Belt et al. |
| 6,280,406 B1 | 8/2001 | Dolecek et al. |
| 6,281,145 B1 | 8/2001 | Deguchi et al. |
| 6,284,142 B1 | 9/2001 | Muller |
| 6,285,155 B1 | 9/2001 | Maske et al. |
| 6,294,094 B1 | 9/2001 | Muller et al. |
| 6,296,450 B1 | 10/2001 | Westberg et al. |
| 6,297,322 B1 | 10/2001 | Ding et al. |
| 6,315,707 B1 | 11/2001 | Smith et al. |
| 6,316,864 B1 | 11/2001 | Ormerod |
| 6,322,488 B1 | 11/2001 | Westberg et al. |
| 6,325,775 B1 | 12/2001 | Thom et al. |
| 6,337,049 B1 | 1/2002 | Tamari |
| RE37,553 E | 2/2002 | Ciavarini et al. |
| 6,343,614 B1 | 2/2002 | Gray et al. |
| 6,348,156 B1 | 2/2002 | Vishnoi et al. |
| 6,361,518 B1 | 3/2002 | Brierton et al. |
| 6,364,857 B1 | 4/2002 | Gray et al. |
| 6,382,923 B1 | 5/2002 | Gray |
| 6,383,158 B1 | 5/2002 | Utterberg |
| 6,406,276 B1 | 6/2002 | Normand et al. |
| 6,409,696 B1 | 6/2002 | Toavs et al. |
| 6,416,293 B1 | 7/2002 | Bouchard et al. |
| 6,419,822 B2 | 7/2002 | Muller et al. |
| 6,455,676 B1 | 9/2002 | Weickert et al. |
| 6,471,855 B1 | 10/2002 | Odak et al. |
| 6,481,980 B1 | 11/2002 | Vandlik et al. |
| 6,489,896 B1 | 12/2002 | Platt et al. |
| 6,497,674 B1 | 12/2002 | Steele et al. |
| 6,497,676 B1 | 12/2002 | Childers et al. |
| 6,503,062 B1 | 1/2003 | Gray et al. |
| 6,514,225 B1 | 2/2003 | Utterberg et al. |
| 6,519,569 B1 | 2/2003 | White et al. |
| 6,520,747 B2 | 2/2003 | Gray et al. |
| 6,524,231 B1 | 2/2003 | Westberg et al. |
| 6,537,445 B2 | 3/2003 | Muller |

| | | |
|---|---|---|
| 6,542,761 B1 | 4/2003 | Jahn et al. |
| 6,558,343 B1 | 5/2003 | Neftel |
| 6,572,604 B1 | 6/2003 | Platt et al. |
| 6,592,542 B2 | 7/2003 | Childers et al. |
| 6,595,948 B2 | 7/2003 | Suzuki et al. |
| 6,603,229 B1 | 8/2003 | Toye, IV |
| 6,604,908 B1 | 8/2003 | Bryant et al. |
| 6,645,166 B2 | 11/2003 | Scheunert et al. |
| 6,645,177 B1 | 11/2003 | Shearn |
| 6,648,861 B2 | 11/2003 | Platt et al. |
| 6,663,359 B2 | 12/2003 | Gray |
| 6,670,323 B1 | 12/2003 | Looker et al. |
| 6,695,803 B1 | 2/2004 | Robinson et al. |
| 6,709,417 B1 | 3/2004 | Houle et al. |
| 6,716,004 B2 | 4/2004 | Vandlik et al. |
| 6,723,062 B1 | 4/2004 | Westberg et al. |
| 6,725,726 B1 | 4/2004 | Adolfs et al. |
| 6,726,656 B2 | 4/2004 | Kamen et al. |
| 6,730,055 B2 | 5/2004 | Bainbridge et al. |
| 6,743,201 B1 | 6/2004 | Dönig et al. |
| 6,746,514 B2 | 6/2004 | Bedingfield et al. |
| 6,749,403 B2 | 6/2004 | Bryant et al. |
| 6,752,172 B2 | 6/2004 | Lauer |
| 6,755,801 B2 | 6/2004 | Utterberg et al. |
| 6,758,975 B2 | 7/2004 | Peabody et al. |
| 6,759,007 B1 | 7/2004 | Westberg et al. |
| 6,764,460 B2 | 7/2004 | Dolecek et al. |
| 6,764,761 B2 | 7/2004 | Eu et al. |
| 6,768,425 B2 | 7/2004 | Flaherty et al. |
| 6,774,517 B2 | 8/2004 | Kowalski et al. |
| 6,790,195 B2 | 9/2004 | Steele et al. |
| 6,790,198 B1 | 9/2004 | White et al. |
| 6,800,054 B2 | 10/2004 | Westberg et al. |
| 6,808,369 B2 | 10/2004 | Gray et al. |
| 6,814,547 B2 | 11/2004 | Childers et al. |
| 6,821,432 B2 | 11/2004 | Metzner |
| 6,828,125 B1 | 12/2004 | Hoffman et al. |
| 6,846,161 B2 | 1/2005 | Kline et al. |
| 6,852,090 B2 | 2/2005 | Burbank et al. |
| 6,869,538 B2 | 3/2005 | Yu et al. |
| 6,905,479 B1 | 6/2005 | Bouchard et al. |
| 6,929,751 B2 | 8/2005 | Bowman, Jr. et al. |
| 6,939,111 B2 | 9/2005 | Huitt et al. |
| 6,949,079 B1 | 9/2005 | Westberg et al. |
| 6,953,323 B2 | 10/2005 | Childers et al. |
| 6,984,218 B2 | 1/2006 | Nayak et al. |
| 7,021,148 B2 | 4/2006 | Kuhn et al. |
| 7,033,539 B2 | 4/2006 | Krensky et al. |
| 7,041,076 B1 | 5/2006 | Westberg et al. |
| 7,044,432 B2 | 5/2006 | Beden et al. |
| 7,049,406 B2 | 5/2006 | Weickert et al. |
| 7,083,719 B2 | 8/2006 | Bowman, Jr. et al. |
| 7,087,036 B2 | 8/2006 | Busby et al. |
| 7,107,837 B2 | 9/2006 | Lauman et al. |
| 7,115,107 B2 | 10/2006 | Delnevo et al. |
| 7,115,228 B2 | 10/2006 | Lundtveit et al. |
| 7,147,613 B2 | 12/2006 | Burbank et al. |
| 7,153,286 B2 | 12/2006 | Busby et al. |
| 7,160,087 B2 | 1/2007 | Fathallah et al. |
| 7,166,231 B2 | 1/2007 | Westberg et al. |
| 7,175,606 B2 | 2/2007 | Bowman, Jr. et al. |
| 7,195,607 B2 | 3/2007 | Westberg et al. |
| 7,211,560 B2 | 5/2007 | Looker et al. |
| 7,232,435 B2 | 6/2007 | Hildebrand et al. |
| 7,236,936 B2 | 6/2007 | White et al. |
| 7,238,164 B2 | 7/2007 | Childers et al. |
| 7,255,680 B1 | 8/2007 | Gharib |
| 7,258,534 B2 | 8/2007 | Fathallah et al. |
| 7,267,661 B2 | 9/2007 | Susi |
| 7,338,472 B2 | 3/2008 | Shearn |
| 7,345,025 B2 | 3/2008 | Symonds et al. |
| 7,347,836 B2 | 3/2008 | Peterson et al. |
| 7,390,311 B2 | 6/2008 | Hildebrand et al. |
| 7,398,183 B2 | 7/2008 | Holland et al. |
| 7,399,637 B2 | 7/2008 | Wright et al. |
| 7,404,809 B2 | 7/2008 | Susi |
| 7,410,475 B2 | 8/2008 | Krensky et al. |
| 7,422,905 B2 | 9/2008 | Clague et al. |
| 7,454,314 B2 | 11/2008 | Holland et al. |
| 7,490,021 B2 | 2/2009 | Holland et al. |
| 7,500,962 B2 | 3/2009 | Childers et al. |
| 7,517,387 B2 | 4/2009 | Chevallet et al. |
| 7,553,295 B2 | 6/2009 | Susi |
| 7,556,616 B2 | 7/2009 | Fathallah et al. |
| 7,618,948 B2 | 11/2009 | Kaemmerer |
| 7,645,258 B2 | 1/2010 | White et al. |
| 7,648,627 B2 | 1/2010 | Beden et al. |
| 7,654,976 B2 | 2/2010 | Peterson et al. |
| 7,662,286 B2 | 2/2010 | Childers et al. |
| 7,699,966 B2 | 4/2010 | Qin et al. |
| 7,789,849 B2 | 9/2010 | Busby et al. |
| 7,815,595 B2 | 10/2010 | Busby et al. |
| 2001/0034502 A1 | 10/2001 | Moberg |
| 2001/0037763 A1 | 11/2001 | Deguchi et al. |
| 2002/0045851 A1 | 4/2002 | Suzuki et al. |
| 2002/0062109 A1 | 5/2002 | Lauer |
| 2002/0072718 A1 | 6/2002 | Brugger et al. |
| 2002/0107474 A1 | 8/2002 | Noack |
| 2002/0147423 A1 | 10/2002 | Burbank et al. |
| 2003/0018395 A1 | 1/2003 | Crnkovich et al. |
| 2003/0028144 A1 | 2/2003 | Duchon et al. |
| 2003/0029451 A1 | 2/2003 | Blair et al. |
| 2003/0042181 A1 | 3/2003 | Metzner |
| 2003/0100882 A1 | 5/2003 | Beden et al. |
| 2003/0136189 A1 | 7/2003 | Lauman et al. |
| 2003/0200812 A1 | 10/2003 | Kuhn et al. |
| 2003/0204162 A1 | 10/2003 | Childers et al. |
| 2003/0217957 A1 | 11/2003 | Bowman et al. |
| 2003/0217961 A1 | 11/2003 | Hopping |
| 2003/0217975 A1 | 11/2003 | Yu et al. |
| 2003/0218623 A1 | 11/2003 | Krensky et al. |
| 2003/0220599 A1 | 11/2003 | Lundtveit et al. |
| 2003/0220605 A1 | 11/2003 | Bowman et al. |
| 2003/0220607 A1 | 11/2003 | Busby et al. |
| 2003/0220608 A1 | 11/2003 | Huitt et al. |
| 2003/0220609 A1 | 11/2003 | Childers et al. |
| 2003/0220627 A1 | 11/2003 | Distler et al. |
| 2004/0010223 A1 | 1/2004 | Busby et al. |
| 2004/0019313 A1 | 1/2004 | Childers et al. |
| 2004/0019320 A1 | 1/2004 | Childers et al. |
| 2004/0031756 A1 | 2/2004 | Suzuki et al. |
| 2004/0064080 A1 | 4/2004 | Cruz et al. |
| 2004/0067161 A1 | 4/2004 | Axelsson |
| 2004/0082903 A1 | 4/2004 | Micheli |
| 2004/0084647 A1 | 5/2004 | Beden et al. |
| 2004/0135078 A1 | 7/2004 | Mandro et al. |
| 2004/0156745 A1 | 8/2004 | Vandlik et al. |
| 2004/0195190 A1 | 10/2004 | Min et al. |
| 2004/0238416 A1 | 12/2004 | Burbank et al. |
| 2005/0054968 A1 | 3/2005 | Giannella |
| 2005/0230292 A1 | 10/2005 | Beden et al. |
| 2006/0079826 A1 | 4/2006 | Beden et al. |
| 2006/0195064 A1 | 8/2006 | Plahey et al. |
| 2007/0112297 A1 | 5/2007 | Plahey et al. |
| 2007/0149913 A1 | 6/2007 | Busby et al. |
| 2007/0193940 A1 | 8/2007 | Duchamp et al. |
| 2007/0213651 A1 | 9/2007 | Busby et al. |
| 2007/0213653 A1 | 9/2007 | Childers et al. |
| 2007/0269340 A1 | 11/2007 | Dannenmaier et al. |
| 2008/0033346 A1 | 2/2008 | Childers et al. |
| 2008/0077068 A1 | 3/2008 | Orr |
| 2008/0208103 A1 | 8/2008 | Demers et al. |
| 2009/0004033 A1 | 1/2009 | Demers et al. |

FOREIGN PATENT DOCUMENTS

| | | |
|---|---|---|
| DE | 100 42 324 | 2/2002 |
| DE | 100 46 651 | 4/2002 |
| DE | 100 53 441 | 5/2002 |
| DE | 101 57 924 | 5/2002 |
| DE | 101 43 137 | 4/2003 |
| EP | 0728509 | 8/1996 |
| EP | 0 947 814 B2 | 10/1999 |
| EP | 0 956 876 A1 | 11/1999 |
| EP | 1529545 | 5/2005 |
| JP | 04-191755 | 7/1992 |
| JP | 06-154314 | 6/1994 |
| JP | 06-002650 | 11/1994 |
| JP | 11-347115 | 12/1999 |

| | | |
|---|---|---|
| JP | 2000-070358 | 3/2000 |
| WO | WO 84/02473 | 7/1984 |
| WO | WO 97/16214 | 5/1997 |
| WO | WO 97/37703 | 10/1997 |
| WO | WO 98/22165 | 5/1998 |
| WO | WO 00/23140 | 4/2000 |
| WO | WO 00/33898 | 6/2000 |
| WO | WO 01/17605 | 3/2001 |
| WO | WO 02/25225 | 3/2002 |

OTHER PUBLICATIONS

Newton IQ Cycler Operator Manual, Part No. 470203 Rev. F, 2000-2006.

Operator's Instructions, Fresenius 90/2 Peritoneal Therapy Cycler, Part No. 470016 Rev. B, 1991.

Gambro®, "DEHP-free cartridge blood sets," © Nov. 2004, Gambro, Inc., Lakewood, CO, 4 pp.

Gambro®, "Prisma® HF 1000, For Increased Filtration Capacity", © Aug. 2001, Gambro Renal Products, Inc., Lakewood, CO, 2 pp.

Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.

Gambro®, "Prismaflex™ anticipating critical care needs and taking our innovative response . . . to new heights," © 2004, Gambro Inc., Lakewood, CO, 8 pp.

Glenn Avolio, "Principles of Rotary Optical Encoders," Sensors Journal of Machine Perception, vol. 10, No. 4, pp. 10-18, 1993.

Manns, Markus et al., "The acu-men: A new device for continuous renal replacement therapy in acute renal failure," Kidney International, vol. 54, pp. 268-274, 1998.

MEDICAL FLUID PUMP SYSTEMS AND RELATED COMPONENTS AND METHODS

CROSS-REFERENCE TO RELATED APPLICATIONS

This application claims the benefit under 35 U.S.C. §119 (e) to U.S. Application Ser. No. 61/162,134, filed on Mar. 20, 2009, which is incorporated by reference herein.

TECHNICAL FIELD

This disclosure relates to medical fluid pump systems and related components and methods.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semipermeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal cavity is periodically infused with sterile aqueous solution, referred to as PD solution or dialysate. The membranous lining of the patient's peritoneum acts as a natural semipermeable membrane that allows diffusion and osmosis exchanges to take place between the solution and the blood stream. These exchanges across the patient's peritoneum result in the removal waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In one aspect of the invention, a medical fluid pump system includes a movable piston head and a cassette. The cassette includes a base defining an opening and a membrane attached to the base covering the opening. The membrane together with the base define a fluid pump chamber, a flow pathway that leads from the fluid pump chamber to an inlet of the cassette, and a flow pathway that leads from the fluid pump chamber to an outlet of the cassette. The cassette is positioned so that the membrane faces the piston head and can be moved by the piston head to change a volume of the fluid pump chamber. An adhesive is disposed between and in contact with the piston head and the membrane. The adhesive has sufficient affinity for the piston head to allow the piston head to retract and deflect the membrane outward to increase the volume of the fluid pump chamber while maintaining adhesive contact with the membrane. The adhesive has substantially greater affinity for the membrane than for the piston head such that the piston head can be retracted in a manner to separate the piston head from the adhesive without separating the adhesive from the membrane.

In another aspect of the invention, a medical fluid delivery cassette includes a base defining an opening and a membrane attached to the base covering the opening. The membrane together with the base define a fluid pump chamber, a flow pathway that leads from the fluid pump chamber to an inlet of the cassette, and a flow pathway that leads from the fluid pump chamber to an outlet of the cassette. A portion of the membrane overlying the fluid pump chamber is moveable relative to the base such that the volume of the fluid pump chamber can be changed by applying a force to the portion of the membrane overlying the fluid pump chamber. An adhesive coating is disposed on an outside surface of the portion of the membrane overlying the fluid pump chamber, and a release layer substantially covers and is releasably attached to the adhesive coating.

In an additional aspect of the invention, a medical fluid delivery method includes adhering a first piston head of a medical system to a membrane of a medical fluid delivery cassette by moving the first piston head into contact with adhesive disposed on a portion the membrane overlying a first fluid pump chamber, and, with the first piston head adhered to the membrane, changing a volume of the first fluid pump chamber by flexing the portion of the membrane overlying the first fluid pump chamber with the first piston head.

Implementations can include one or more of the following features.

In some implementations, the piston head is adapted to be moved away from the cassette with a force sufficient to overcome the affinity between the piston head and the adhesive such that the piston head can be separated from the membrane.

In certain implementations, the piston head is arranged to be moved a distance of at least 1.5 centimeters away from a plane in which the membrane lies when the membrane is not deformed by the piston head.

In some implementations, the system includes a wall adjacent the cassette, and the piston head can be retracted beyond an outer surface of the wall.

In certain implementations, the piston head includes (e.g., is formed of) polyoxymethylene and the membrane includes (e.g., is formed of) a low density polyolefin.

In some implementations, the adhesive includes (e.g., is formed of) synthetic rubber (e.g., a double coated synthetic rubber tape).

In certain implementations, an adhesion strength of the adhesive to polyester is about 89 Oz./in. (about 97 N/100 mm), as tested using the ASTM D3330 test (90 degree, 2 mil Al foil, 72 hour RT).

In some implementations, an adhesion strength of the adhesive to polypropylene is about 85 Oz./in. (about 93 N/100 mm), as tested using the ASTM D3330 test (90 degree, 2 mil Al foil, 72 hour RT).

In certain implementations, an adhesion strength of the adhesive to polycarbonate is about 101 Oz./in. (about 110 N/100 mm), as tested using the ASTM D3330 test (90 degree, 2 mil Al foil, 72 hour RT).

In some implementations, an adhesion strength of the adhesive 161 to stainless steel is about 97 Oz./in. (about 106 N/100 mm), as tested using the ASTM D3330 test (90 degree, 2 mil Al foil, 72 hour RT).

In certain implementations, an adhesion strength of the adhesive to the membrane is substantially greater than an adhesion strength of the adhesive to the piston head.

In some implementations, the adhesive includes a first layer of adhesive in contact with the membrane and a second layer of adhesive in contact with the piston head.

In certain implementations, the medical fluid pump system further includes a base layer (e.g., a substantially liquid impermeable base layer) disposed between the first and second layers of adhesive.

In some implementations, the first layer of adhesive is biocompatible and the second layer of adhesive is bioincompatible.

In certain implementations, the piston head is movable in a direction substantially perpendicular to the cassette.

In some implementations, the piston head can be separated from the adhesive by moving the piston head in the direction substantially perpendicular to the cassette.

In certain implementations, the piston head is configured to be rotated relative to the cassette.

In some implementations, the piston head can be separated from the adhesive by rotating the piston head relative to the cassette.

In certain implementations, the base of the cassette is a molded tray-like base.

In some implementations, the adhesive is disposed on a portion of the membrane overlying the fluid pump chamber.

In certain implementations, the adhesive is substantially uniformly disposed on the portion of the membrane overlying the fluid pump chamber.

In some implementations, the medical system includes first and second movable piston heads, and the membrane together with the base defines first and second fluid pump chambers, flow pathways that lead from the first and second fluid pump chambers to the inlet of the cassette, and flow pathways that lead from the first and second fluid pump chambers to the outlet of the cassette. The cassette is positioned so that the membrane faces the first and second piston heads and can be moved by the first and second piston heads to alter volumes of the first and second fluid pump chambers, and adhesive is disposed between and in contact with the first and second piston heads and the membrane. The adhesive has sufficient affinity for the first and second piston heads to allow the first and second piston heads to retract and deflect the membrane outward to increase the volumes of the first and second fluid pump chambers while maintaining adhesive contact with the membrane. The adhesive has substantially greater affinity for the membrane than for the first and second piston heads such that the first and second piston heads can be retracted in a manner to separate the first and second piston heads from the adhesive without separating the adhesive from the membrane.

In certain implementations, the medical fluid pump system is a dialysis system (e.g., a peritoneal dialysis system).

In some implementations, the adhesive coating is produced by applying the release layer carrying adhesive to the membrane.

In certain implementations, the release layer is release paper (e.g., a wax-coated paper).

In some implementations, the adhesive coating is disposed on a portion of the membrane that is contacted by a piston head of a medical fluid pump system during use.

In certain implementations, the release layer is removable from the adhesive coating to expose at least a portion of the adhesive coating.

In some implementations, the release layer includes a pull tab that extends beyond an outer boundary of the adhesive.

In certain implementations, the membrane includes a low density polyolefin.

In some implementations, the medical fluid delivery cassette is configured for use with a dialysis machine (e.g., a peritoneal dialysis machine).

In certain implementations, the medical fluid delivery cassette is disposable.

In some implementations, the adhesive coating has a greater affinity for the membrane than for a piston head of a medical fluid pumping system when the cassette is in use with the medical fluid pumping system such that the piston head can be retracted in a manner to separate the piston head from the adhesive without separating the adhesive from the membrane.

In certain implementations, the adhesive coating includes first and second layers of adhesive, and the first layer of adhesive is in contact with the membrane.

In some implementations, the adhesive has a greater affinity for the membrane than for the first piston head such that the first piston head can be retracted in a manner to separate the first piston head from the adhesive without separating the adhesive from the membrane.

In certain implementations, flexing the portion of the membrane overlying the first fluid pump chamber includes moving the first piston head away from the cassette with a force that does not exceed the affinity between the membrane and the adhesive.

In some implementations, the medical fluid delivery method further includes decoupling the first piston head from the membrane by moving the first piston head relative to the cassette.

In certain implementations, the adhesive remains attached to the membrane after decoupling the first piston head from the membrane.

In some implementations, the medical fluid delivery method further includes decoupling the first piston head from the membrane by moving the piston head in a direction substantially perpendicular to the cassette.

In certain implementations, the medical fluid delivery method further includes decoupling the first piston head from the membrane by rotating the piston head relative to the cassette.

In some implementations, the medical fluid delivery method further includes adhering a second piston head to the membrane by moving the second piston head into contact with adhesive disposed on a portion of the membrane overlying a second fluid pump chamber and, with the second piston head adhered to the membrane, changing a volume of the second fluid pump chamber by flexing the portion of the membrane overlying the second fluid pump chamber with the second piston head.

In certain implementations, the medical fluid delivery method further includes disposing the adhesive on the membrane by applying a release layer carrying adhesive to the membrane.

In some implementations, the medical fluid delivery method further includes removing the release layer from the adhesive.

In certain implementations, removing the release layer includes pulling on a pull tab of the release paper, where the pull tab extends beyond an outer boundary of the adhesive prior to removing the release layer from the adhesive.

Implementations can include one or more of the following advantages.

In some implementations, the PD system includes an adhesive disposed between the piston head and the membrane.

This arrangement permits the piston head to be moved in a direction away from the cassette to draw dialysate into the cassette without extensive use of a vacuum system. For example, while the PD system may include a vacuum system to deflate inflatable valves that are used to direct fluid through desired pathways of the cassette, the membrane of the cassette in the region of the pump chamber can be attached to the piston head using only adhesive. By using adhesive, as opposed to vacuum pressure, to secure the membrane of the cassette to the piston head, the likelihood of fluid being pulled through the membrane (e.g., through very small holes in the membrane) is substantially reduced or eliminated. Additionally or alternatively, the level of noise produced by the PD system during operation can be substantially reduced relative to certain prior PD systems that use vacuum pressure retract the cassette membrane in the region of the pump chamber as the piston head is retracted. In addition, the use of adhesive to secure the membrane of the cassette to the piston head can reduce the overall cost and complexity of manufacturing the PD system.

In certain implementations, the piston head is adhesively attached to the membrane of the cassette and can draw the membrane away from the cassette to draw dialysate into the cassette. The adhesive attachment between the piston head and the membrane can result in a substantially direct correlation between the piston head position and the volume drawn into the cassette. Thus, adhesively attaching the piston head to the membrane can improve the speed and accuracy of volumetric calculations of dialysate drawn into the cassette. Additionally or alternatively, if any holes (e.g., pinholes) were to develop in the portion of the membrane to which the adhesive is attached, the adhesive could act as a seal and thus reduce the likelihood that fluid will leak out of the cassette.

In certain implementations, the adhesion strength or affinity of the adhesive to the membrane of the cassette is greater than the adhesion strength or affinity of the adhesive to the piston head. In such a configuration, the piston head can be moved away from the membrane by a sufficient distance and with a sufficient force to detach the piston head from the adhesive without detaching the adhesive from the membrane. The piston head can, for example, be retracted with a force greater than the adhesion strength of the adhesive to the piston head but less than the adhesion strength of the adhesive to the membrane of the cassette to detach the piston head from the adhesive while retaining the attachment between the adhesive and the membrane of the cassette. The particular material properties of the adhesive, cassette membrane, and piston head inhibit or eliminate adhesive from remaining attached to the piston head upon detachment of the piston head from the membrane and can thus reduce or prevent adhesive build-up in the PD system over time.

In some implementations, the cassette is disposable. In such implementations, the cassette, along with adhesive retained on the cassette, can be discarded after use. Such a disposable cassette can reduce the need for the user to remove or otherwise handle the adhesive.

In certain implementations, a release layer (e.g., a release paper) covers and is releasably attached to adhesive on the cassette. The release layer can be removed to expose the adhesive before use. The release layer can help to prevent debris and contaminants from collecting on the adhesive prior to use of the cassette.

Other aspects, features, and advantages will be apparent from the description and drawings, and from the claims.

DETAILED DESCRIPTION

Figure 1:
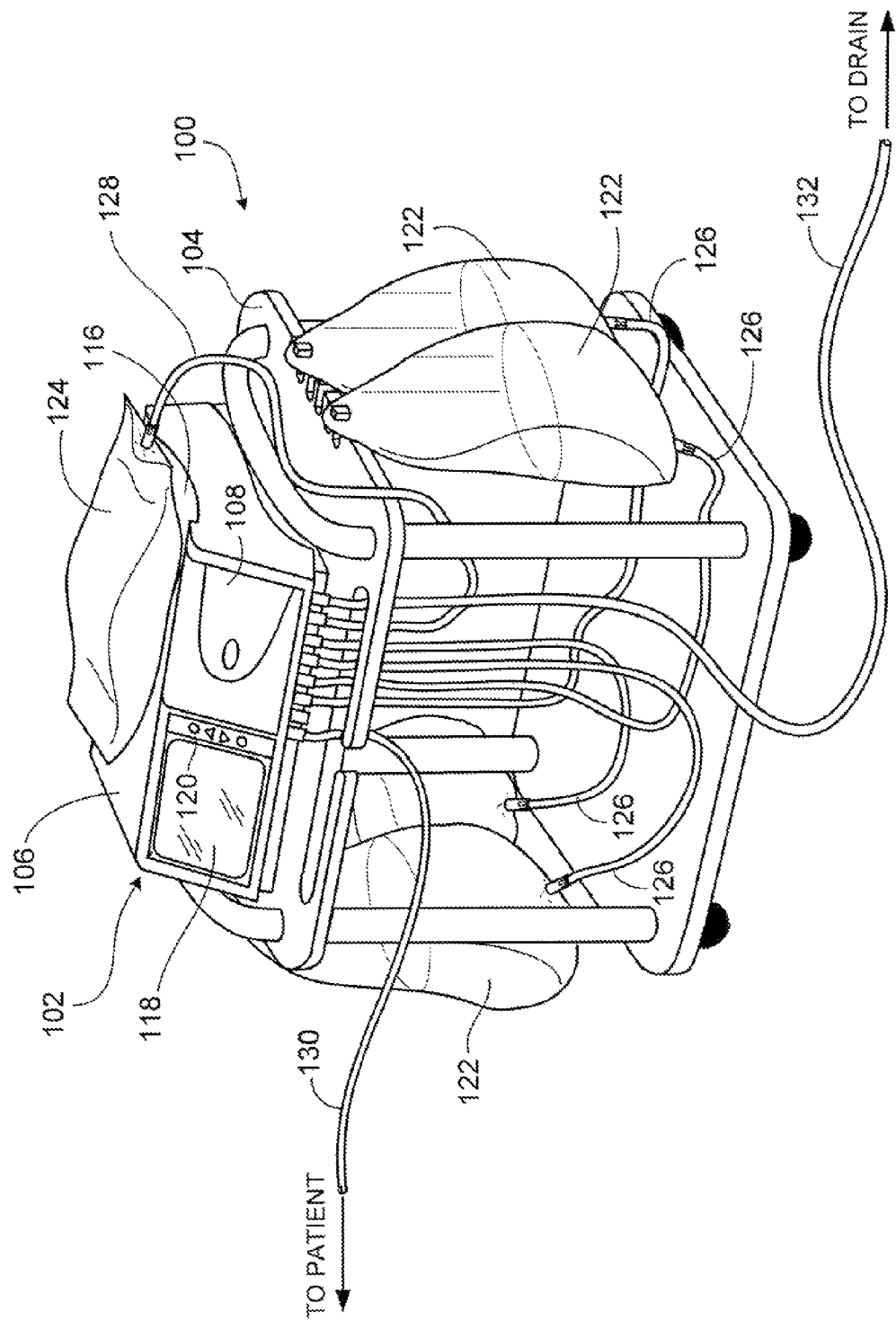
FIG. 1 is a perspective view of a PD system.
Figure 2:
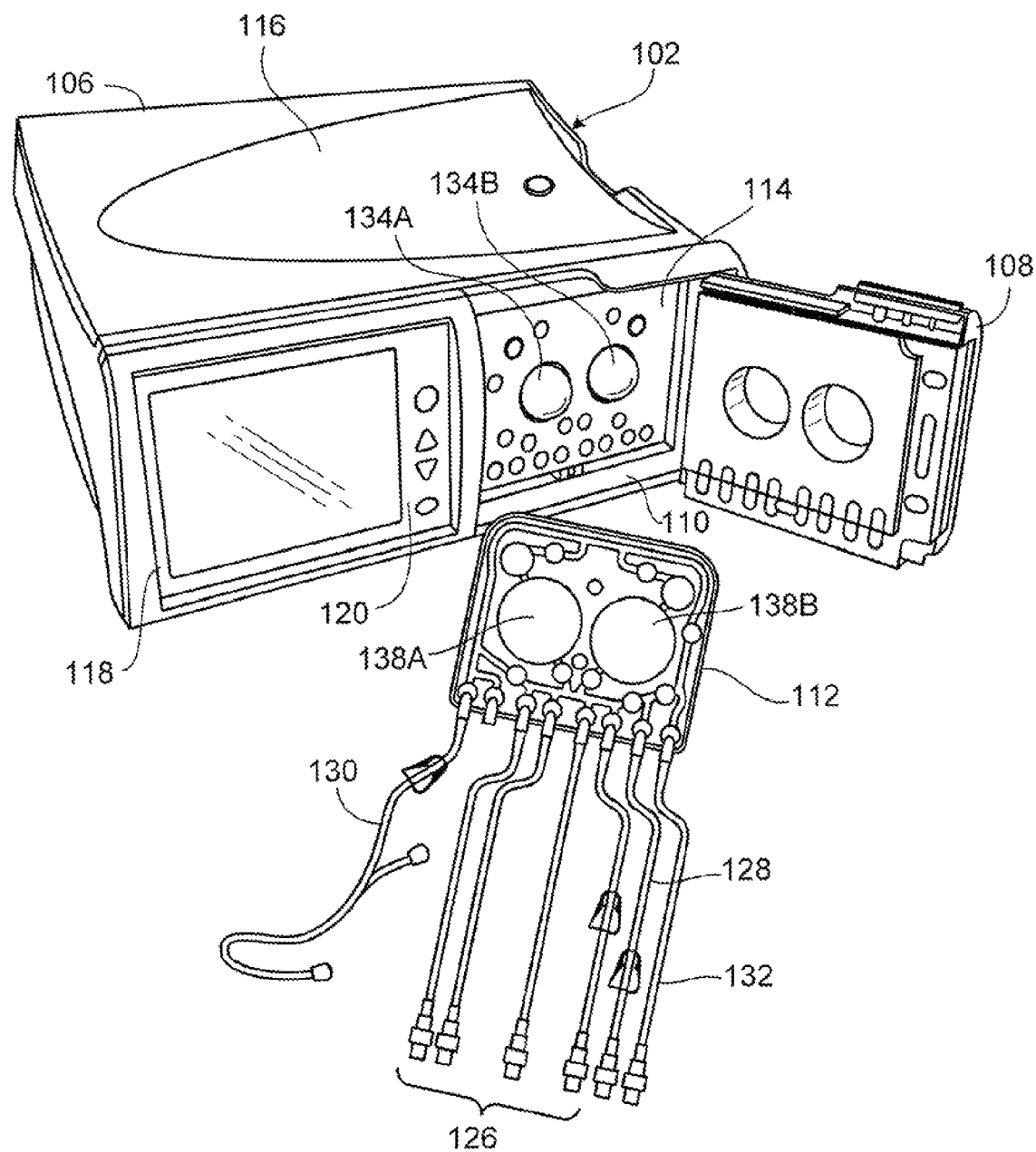
FIG. 2 is a perspective view of a PD cycler and PD cassette of the PD system of FIG. 1. A door of the PD cycler is in the open position to show the inner surfaces of the PD cycler that interface with the PD cassette during use.

Referring to FIG. 1, a peritoneal dialysis ("PD") system 100 includes a PD cycler (also referred to as a PD machine) 102 seated on a cart 104. Referring also to FIG. 2, the PD cycler 102 includes a housing 106, a door 108, and a cassette interface 110 that mates with a disposable PD cassette 112 when the cassette 112 is disposed within a cassette enclosure 114 formed between the cassette interface 110 and the closed door 108. A heater tray 116 is positioned on top of the housing 106. The heater tray 116 is sized and shaped to accommodate a bag of PD solution (e.g., a 5 liter bag of PD solution). The PD cycler 102 also includes a touch screen 118 and additional control buttons 26 that can be operated by a user (e.g., a patient) to allow, for example, set-up, initiation, and/or termination of a PD treatment.

PD solution bags 122 are suspended from fingers on the sides of the cart 104, and a heater bag 124 is positioned in the heater tray 116. The PD solution bags 122 and the heater bag 124 are connected to the cassette 112 via PD solution bag lines 126 and a heater bag line 128, respectively. The PD solution bag lines 126 can be used to pass PD solution from PD solution bags 122 to the cassette 112 during use, and the heater bag line 128 can be used to pass PD solution back and forth between the cassette 112 and the heater bag 124 during use. In addition, a patient line 130 and a drain line 132 are connected to the cassette. The patient line 130 can be connected to a patient's abdomen via a catheter and can be used to pass PD solution back and forth between the cassette 112 and the patient during use. The drain line 132 can be connected to a drain or drain receptacle and can be used to pass PD solution from the cassette 112 to the drain or drain receptacle during use.

Figure 3:
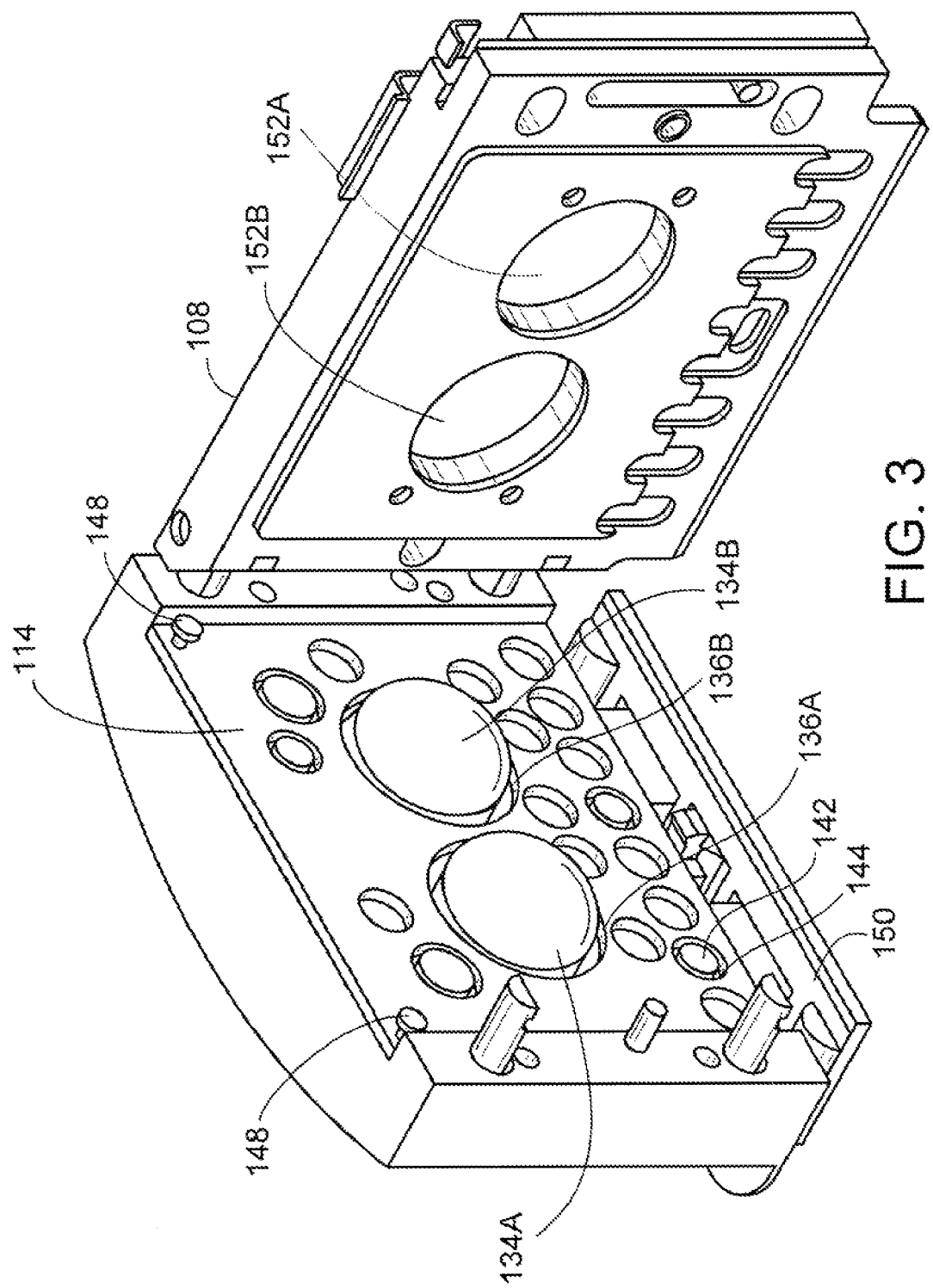
FIG. 3 is a perspective view of a cassette compartment of the PD cycler of FIGS. 1 and 2.

FIG. 3 shows a more detailed view of the cassette interface 110 and the door 108 of the PD cycler 102. As shown, the PD cycler 102 includes pistons with substantially hemispherical piston heads 134A, 134B that can be axially moved within piston access ports 136A, 136B formed in the cassette interface 110. The piston heads 134A, 134B are made of polyoxymethylene (marketed under the tradename Delrin available from Dupont of Wilmington, Del.). The hemispherical shape of the piston heads 134A, 134B can be achieved using machining techniques. Alternatively or additionally, the hemispherical shape of the piston heads 134A, 134B can be formed using molding or casting techniques. The pistons include piston shafts that are coupled to motors that can be operated to move the piston heads 134A, 134B axially inward and outward within the piston access ports 136A, 136B. As discussed below, when the cassette 112 (shown in FIGS. 2 and 4-7) is positioned within the cassette enclosure 114 with the door 108 closed, the piston heads 134A, 134B of the PD cycler 102 align with pump chambers 138A, 138B of the cassette 112. The piston heads 134A, 134B, as described in greater detail below, can be adhered to portions of a membrane 140 overlying the pump chambers 138A, 138B of the cassette 112. As a result, the piston heads 134A, 134B can be moved in the direction of the cassette 112 to force the membrane 140 into the volume defined by the pump chambers 138A, 138B, causing the volume defined by the pump chambers to decrease and forcing fluid out of the pump chambers 138A, 138B. The piston heads 134A, 134B can also be retracted away from the cassette 112 and out of the volume defined by the pump chambers 138A, 138B such that the volume defined by the pump chambers 138A, 138B increases and fluid is drawn into the pump chambers 138A, 138B.

The PD cycler 102 also includes multiple inflatable members 142 positioned within inflatable member access ports 144 in the cassette interface 110. The inflatable members 142 align with depressible dome regions 146 of the cassette 112 when the cassette 112 is positioned within the cassette enclosure 114. While only one of the inflatable members 142 is labeled in FIG. 3, it should be understood that the PD cycler 102 includes an inflatable member associated with each of the depressible dome regions 146 of the cassette 112 (shown in FIG. 5). The inflatable members 142 act as valves to direct fluid through the cassette 112 in a desired manner during use. In particular, the inflatable members 142 bulge outward beyond the surface of cassette interface 110 and into contact with the depressible dome regions 146 of the cassette 112 when inflated, and retract into the inflatable member access ports 144 and out of contact with the cassette 112 when deflated. By inflating certain inflatable members 142 to depress their associated dome regions 146 on the cassette 112, certain fluid flow paths within the cassette 112 can be blocked off. Thus, fluid can be pumped through the cassette 112 by actuating the piston heads 134A, 134B, and can be guided along desired flow paths within the cassette 112 by selectively inflating and deflating the inflatable members 142.

Still referring to FIG. 3, locating pins 148 extend from the cassette interface 110. When the door 108 is in the open position, the cassette 112 can be loaded onto the cassette interface 110 by positioning the top portion of the cassette 112 under the locating pins 148 and pushing the bottom portion of the cassette 112 toward the cassette interface 110. The cassette 112 is dimensioned to remain securely positioned between the locating pins 148 and a lower ledge 150 extending from the cassette interface 110 to allow the door 108 to be closed over the cassette 112. The locating pins 148 help to ensure that the pump chambers 138A, 138B of the cassette 112 are aligned with the piston heads 134A, 134B when the cassette 112 is positioned in the cassette enclosure 114 between the closed door 108 and the cassette interface 110.

The door 108 defines recesses 152A, 152B that substantially align with the piston heads 134A, 134B when the door 108 is in the closed position. When the cassette 112 is positioned within the cassette enclosure 114, hemispherical projections 154A, 154B of the cassette 112 (shown in FIG. 4), which partially define the pump chambers 138A, 138B, fit within the recesses 152A, 152B. In this configuration, the portions of the door 108 forming the recesses 152A, 152B can support the hemispherical projections 154A, 154B while the planar surface of the door 108 can counteract the force of the inflatable members 142 and thus allow the inflatable members 142 to actuate the depressible dome regions 146 on the cassette 112.

The PD cycler 102 includes various other features not described here. Further details regarding the PD cycler 102 and its various components can be found in U.S. Patent Application Publication No. 2007/0112297, which is incorporated by reference herein.

Figure 4:
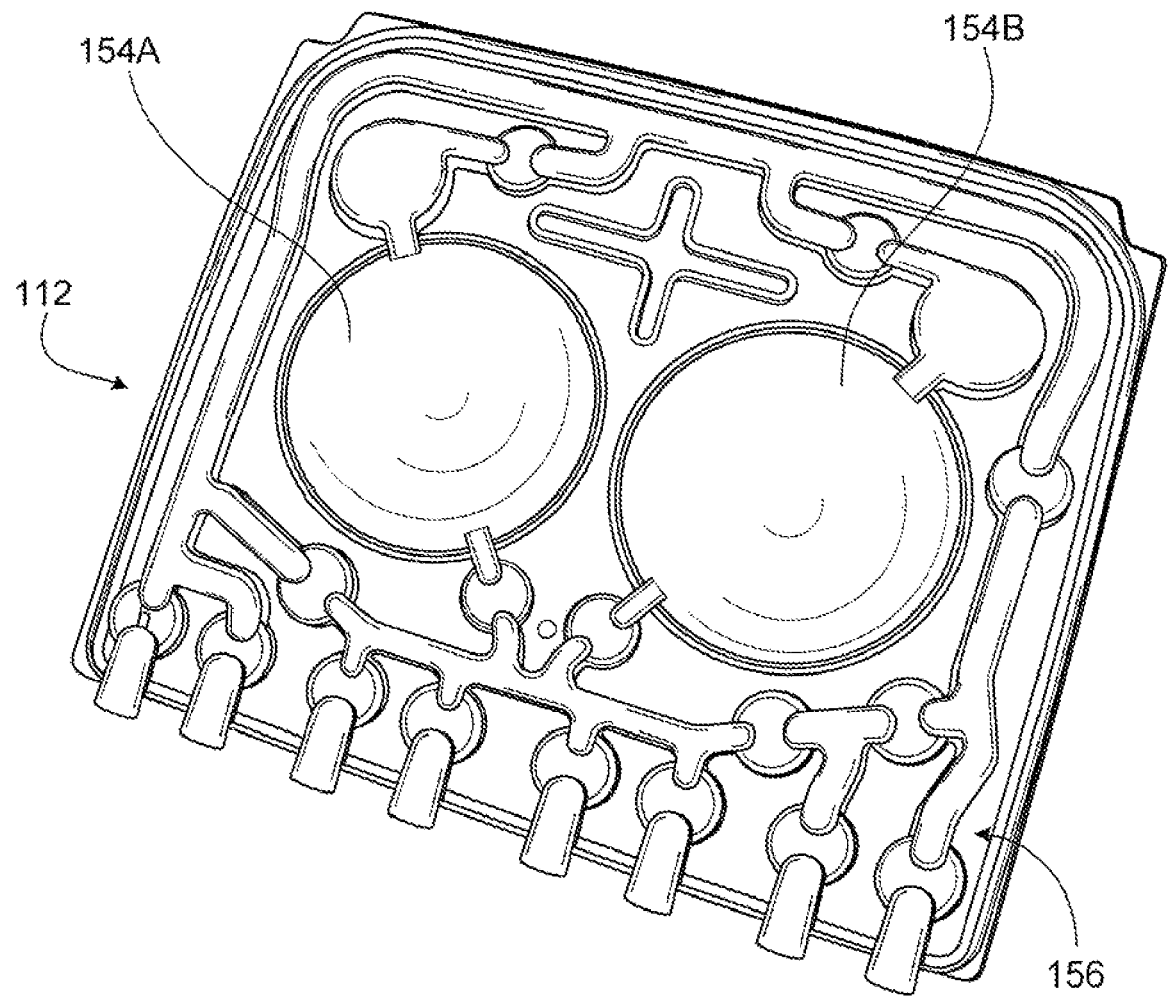
FIG. 4 is a perspective view from a rigid base side of the PD cassette of the PD system of FIG. 1.
Figure 5:
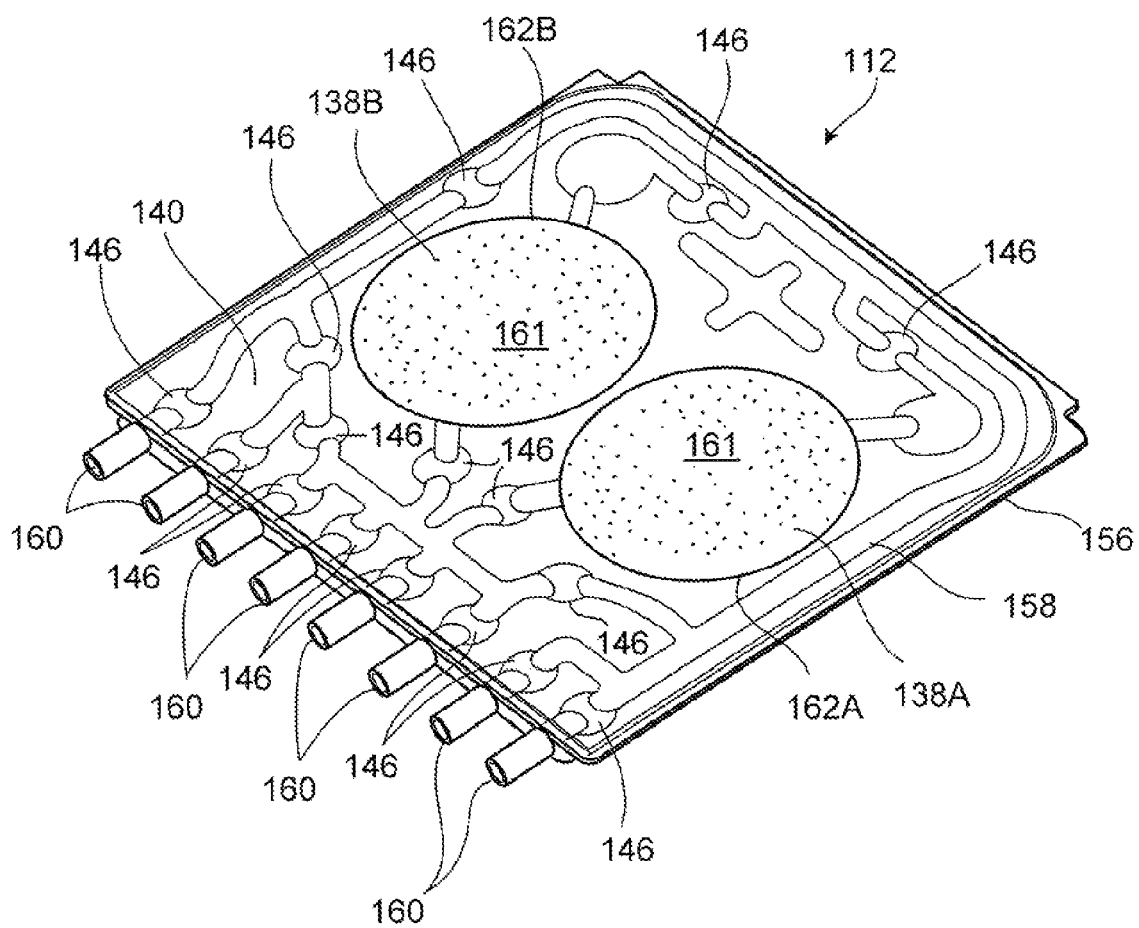
FIG. 5 is a perspective view from a flexible membrane side of the PD cassette of the PD system of FIG. 1.
Figure 6:
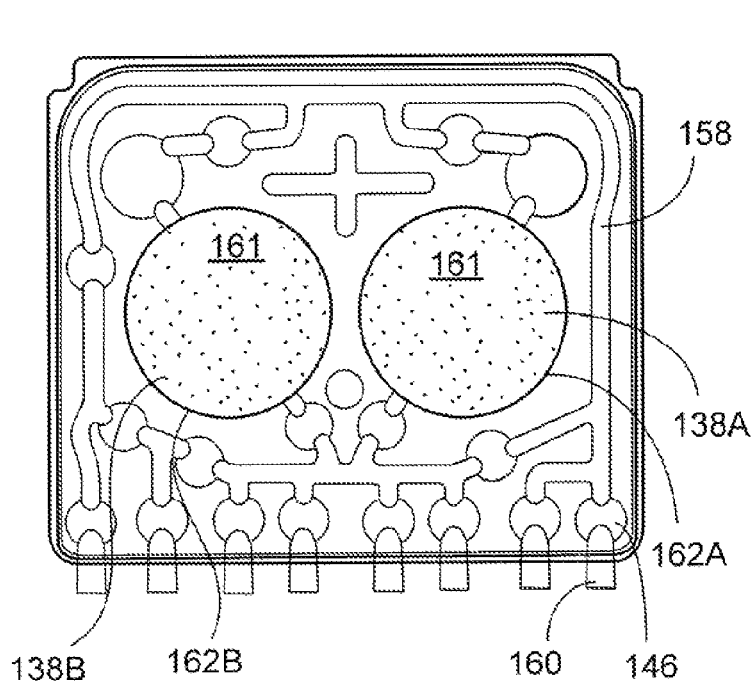
FIG. 6 is a plan view from the membrane side of the PD cassette of the PD system of FIG. 1.
Figure 7:
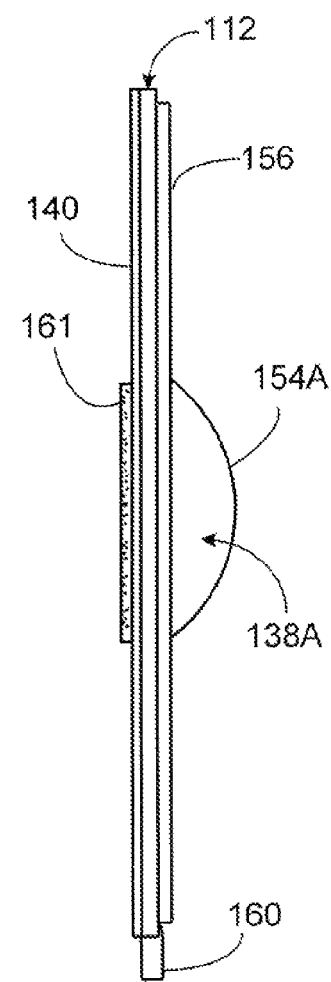
FIG. 7 is a side view of the PD cassette of the PD system of FIG. 1, showing adhesive disposed on the portion of the membrane overlying a pump chamber of the cassette.

Referring to FIGS. 4-7, the cassette 112 includes a tray-like rigid base 156 and the flexible membrane 140, which is attached to (e.g., thermally bonded to, adhered to) the periphery of the base 156. The base is made of polypropylene, and can be formed using machining, molding, and/or casting techniques. As shown in FIGS. 4 and 7, the hemispherical, hollow projections 154A, 154B of the base 156 are substantially symmetrically positioned with respect to the center vertical axis of the cassette 112. The hemispherical projections 154A, 154B extend away from the membrane 140 and are sized and shaped to fit within the recesses 152A, 152B in the door 108 of the PD cycler 102. The membrane 140 cooperates with the base 156 to form the pump chambers 138A, 138B. In particular, the volume between the membrane 140 and the projections 154A, 154B define the pump chambers 138A, 138B. The base 156 further includes raised structural features that extend toward and into contact with the inner surface of the membrane 140. The membrane 140 cooperates with the raised structural features extending from the base 156 to form a series of fluid pathways 158 and the multiple, depressible dome regions 146, which are widened (e.g., substantially circular) portions of the fluid pathways. At each depressible dome region 146, the membrane 140 can be deflected to contact the base 156. Such contact can substantially impede (e.g., prevent) the flow of PD solution along the pathway 158 associated with that dome region 146 during use. Thus, as described in further detail below, the flow of PD solution through the cassette 112 can be controlled through the selective depression of the depressible dome regions 146 by selectively inflating the inflatable members 142 of the PD cycler 102.

The rigidity of the base 156 helps to hold the cassette 112 in place within the cassette enclosure 114 of the PD cycler 102 and to prevent the hemispherical projections 154A, 154B and the other raised features of the cassette 112 from flexing and deforming in response to changes in pressure within the cassette 112 during use. The rigidity of the base 156 also allows the hemispherical projections 154A, 154B to resist deformation by the piston heads 134A, 134B during use.

The fluid pathways 158 in the cassette 112 lead from the pumping chambers 138A, 138B to connectors 160 positioned along the bottom edge of the cassette 112. The connectors 160 are positioned asymmetrically along the width of the cassette 112. The asymmetrical positioning of the connectors 160 helps to ensure that the cassette 112 will be properly positioned in the cassette enclosure 114 with the membrane 140 and of the cassette 112 facing the cassette interface 110. The connectors 160 are configured to receive fittings on the ends of the PD solution bag lines 126, the heater bag line 128, the patient line 130, and the drain line 132. These fittings are double male fittings. One end of the fitting can be inserted into and bonded to its respective line and the other end can be inserted into and bonded to its associated connector 160. By permitting the PD solution bag lines 126, the heater bag line 128, the patient line 130, and the drain line 132 to be connected to the cassette, as shown in FIGS. 1 and 2, the connectors 160 allow PD solution to flow into and out of the cassette 112 during use.

Still referring to FIGS. 4-7, the membrane 140 of the cassette 112 includes three layers. The inner and outer layers of the laminate are formed of a compound that is made up of 60 percent Septon® 8004 thermoplastic rubber (i.e., hydrogenated styrenic block copolymer) and 40 percent ethylene. The middle layer is formed of a compound that is made up of 25 percent Tuftec® H1062(SEBS: hydrogenated styrenic thermoplastic elastomer), 40 percent Engage® 8003 polyolefin elastomer (ethylene octene copolymer), and 35 percent Septon® 8004 thermoplastic rubber (i.e., hydrogenated styrenic block copolymer). The thickness of the membrane 140 is selected so that the membrane 140 has sufficient flexibility to flex toward the base 156 in response to the force applied to the membrane 140 by the piston heads 134A, 134B. For example, the membrane 140 can be about 0.100 inch to about 0.150 inch in thickness.

Adhesive 161 is disposed on regions 162A, 162B of the membrane 140 that overlie the pump chambers 138A, 138B. The adhesive 161 is a double coated synthetic rubber adhesive tape manufactured by 3M as part number 9443NP. The properties of the adhesive 161 allow the adhesive 161 to achieve a temporary adhesive attachment with the piston heads 134A, 134B when the piston heads 134A, 134B are brought into contact with the adhesive regions during use. The attachment between the adhesive 161 and the piston heads 134A, 134B is sufficiently strong to allow the adhesive to remain attached to the piston heads 134A, 134B as the piston heads 134A, 134B are reciprocated during use. At the same time, the attachment between the adhesive 161 and the piston heads 134A, 134B can be readily broken by retracting the piston heads 134A, 134B by a greater distance than they are retracted during treatment and with a force that exceeds the adhesion force between the adhesive 161 and the piston heads 134A, 134B.

The adhesion strength of the adhesive 161 to polyester is about 89 Oz./in. (about 97 N/100 mm), as tested using the ASTM D3330 test (90 degree, 2 mil Al foil, 72 hour room temperature (RT)). The adhesion strength of the adhesive 161 to polypropylene is about 85 Oz./in. (about 93 N/100 mm), as tested using the ASTM D3330 test (90 degree, 2 mil Al foil, 72 hour RT). The adhesion strength of the adhesive 161 to polycarbonate is about 101 Oz./in. (about 110 N/100 mm), as tested using the ASTM D3330 test (90 degree, 2 mil Al foil, 72 hour RT). The adhesion strength of the adhesive 161 to stainless steel is about 93 Oz./in. (about 101 N/100 mm), as tested using the ASTM D3330 test (90 degree, 2 mil Al foil, 15 minute RT). The adhesion strength of the adhesive 161 to stainless steel is about 97 Oz./in. (about 106 N/100 mm), as tested using the ASTM D3330 test (90 degree, 2 mil Al foil, 72 hour RT). The adhesion strength of the adhesive 161 to stainless steel is about 126 Oz./in. (about 137 N/100 mm), as tested using the ASTM D3330 test (90 degree, 2 mil Al foil, 72 hour 158° F. (70° C.)). The adhesion strength of the adhesive 161 to stainless steel is about 206 Oz./in. (about 224 N/100 mm), as tested using the ASTM D3330 test (180 degree, 2 mil Al foil, 72 hour RT).

During use, the cassette 112 is secured within the cassette enclosure 114 by positioning the adhesive-carrying side of the cassette 112 adjacent to the cassette interface 110 of the PD cycler 102 and closing the door 108 over the cassette 112. As noted above, the piston heads 134A, 134B align with the pump chambers 138A, 138B of the cassette 112 when the cassette 112 is positioned in the cassette enclosure 114 between the cassette interface 110 and the closed door 108. Thus, with the cassette 112 secured in the cassette enclosure 114, the piston heads 134A, 134B can extend into the enclosure 114 to contact the adhesive 161 disposed on regions 162A, 162B of the flexible membrane 140 and become temporarily adhesively attached to the membrane 140 of the cassette 112. The adhesive 161, the material of the piston heads 134A, 134B, and the material of the membrane 140 are selected so that the adhesive 161 has a greater adhesion or affinity to the membrane 140 than to the piston heads 134A, 134B. The adhesive attachment between the piston heads 134A, 134B and the membrane 140 causes the regions 162A, 162B of the membrane 140 overlying the pump chambers 138A, 138B to move along with the piston heads 134A, 134B, and thus allows PD solution to be drawn into or forced out of the pump chambers of the cassette 112 in response to piston head movement during treatment. Movement of those regions 162A, 162B of the membrane 140 overlying the pump chambers 138A, 138B (e.g., through movement of piston heads 134A, 134B) changes the internal volume of the pump chambers 138A, 138B. For example, movement of the membrane 140 toward the rigid base 156 decreases the fluid volume stored in each of the pump chambers 138A, 138B, and thus forces some of the PD solution out of the cassette 112 during treatment. Similarly, movement of the membrane 140 away from the base 156 increases the fluid volume stored in the pump chambers 138A, 138B, and thus draws PD solution into the cassette 112 during treatment.

By retracting the piston heads 134A, 134B farther than they are retracted during treatment (i.e., farther than they are retracted to draw fluid into the pump chambers 138A, 138B during treatment) and with a force that exceeds the adhesion force between the piston heads 134A, 134B and the adhesive 161, the piston heads 134A, 134B can be detached from the adhesive 161 and the membrane 140. The piston heads 134A, 134B can, for example, be fully retracted into the piston access ports 136A, 136B to detach the piston heads 134A, 134B from the adhesive 161 and the membrane 140. In some cases, the piston heads 134A, 134B are retracted at least about 1.0 centimeters (e.g., at least about 1.5 centimeters, about 1.0 centimeters to about 2.5 centimeters, about 1.5 centimeters) away from the plane in which the membrane 140 lies in its undeformed state with the cassette 112 positioned in the cassette enclosure 114. Retracting the piston heads 134A, 134B to this position can help to ensure that the piston heads 134A, 134B detach from the adhesive 161.

The movement of the piston heads 134A, 134B away from the cassette 112 exerts a tensile stress on the adhesive 161. The piston heads 134A, 134B remain substantially adhered to the adhesive 161 if the tensile forces exerted by the piston heads 134A, 134B are less than the adhesion strength of the adhesive 161 to the piston heads 134A, 134B and/or the piston heads 134A, 134B are retracted by a distance less than the distance required to detach the piston heads 134A, 134E from the adhesive 161. The piston heads 134A, 134B detach from the adhesive 161 if the tensile forces exerted by the piston heads 134A, 134B are greater than the adhesion strength of the adhesive 161 to the piston heads 134A, 134B and the piston heads 134A, 134B are retracted by a sufficient distance to detach the piston heads 134A, 134B from the adhesive 161.

To permit the piston heads 134A, 134B to be detached from the adhesive 161 while the adhesive 161 remains attached to the membrane 140 of the cassette 112, the adhesive 161, the piston heads 134A, 134B, and the membrane 140 are formed of materials such that the adhesion strength or affinity of the membrane 140 to the adhesive 161 is greater than the adhesion strength or affinity of the piston heads 134A, 134B to the adhesive 161. To reduce the likelihood that the adhesive 161 will detach from the membrane 140 (and remain attached to the piston heads 134A, 134B) while attempting to detach the piston heads 134A, 134B from the adhesive (i.e., by retracting the piston heads 134A, 134B), the adhesive 161, the piston heads 134A, 134B, and the membrane 140 are formed of materials such that the adhesion strength or affinity of the adhesive 161 to the membrane 140 is substantially greater (e.g., at least about two times greater (e.g., about two to about three times greater)) than the adhesion strength or affinity of the adhesive 161 to the piston heads 32A, 23B.

As a result of the selected materials of the adhesive 161, the piston heads 134A, 134B, and the membrane 140, the piston heads 134A, 134B can be detached from the adhesive 161 in a manner similar to that in which a 3M Post-It® note is detached from a surface (e.g., desktop or sheet of paper). The material selection can, for example, ensure that an insignificant amount of adhesive (e.g., no adhesive) remains attached to the piston heads 134A, 134B after the piston heads 134A, 134B are detached from the adhesive 161 and the membrane 140.

In some implementations, the adhesive 161 is capable of maintaining contact with the piston heads 134A, 134B for up to 24 hours at a pump speed of about 200 ml/min to about 600 ml/min.

In certain implementations, the adhesive 161 is disposed substantially uniformly over regions 162A, 162B. Such a substantially uniform distribution of the adhesive 161 can reduce the likelihood that the membrane 140 will separate or decouple from the piston heads 134A, 134B during normal operation. Additionally or alternatively, such a substantially uniform distribution of adhesive can improve the accuracy in calculating the volume of pump chambers 138A, 138B based on the position of the piston heads 134A, 134B, which can be used to closely track the volume of PD solution pumped out of and drawn into the pump chambers 138A, 138B during treatment.

In addition to securing the piston heads 134A, 134B to the membrane 140 of the cassette 112, the adhesive 161 can reduce the likelihood of fluid intrusion into the PD cycler 102 during use. For example, because the adhesive 161, rather than vacuum pressure, is used to retract the portions of the membrane 140 overlying the pump chambers 138A, 138B in order to draw fluid into the pump chambers 138A, 138B, the possibility of fluid being drawn through the membrane 140 as a result of excessive vacuum pressure is eliminated. In addition, in some cases, the adhesive 161 acts as a substantially impermeable layer that restricts (e.g., prevents) PD solution from passing through the cassette 112 into the PD cycler 102 in regions 162A, 162B. For example, to the extent that the membrane 140 is semi-permeable or becomes semi-permeable (e.g., through repeated flexing during use), the adhesive 161 can form a substantially liquid tight seal with the membrane 140 across regions 162A, 162B of the membrane 140.

Figure 8:
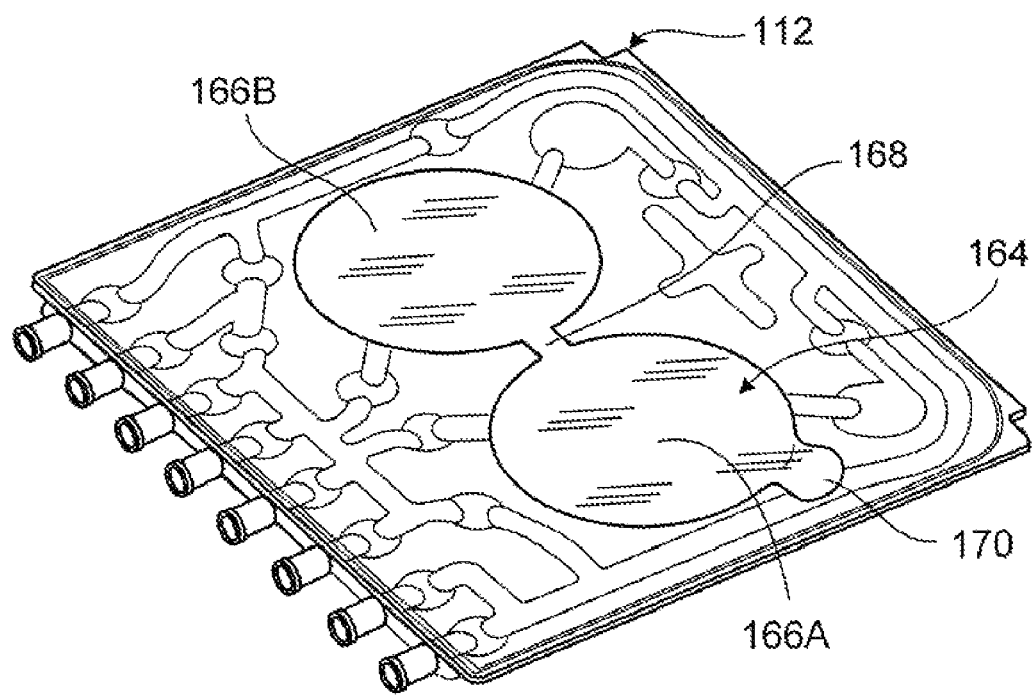
FIG. 8 is a perspective view from the membrane side of the PD cassette of the PD system of FIG. 1 with eyeglass-shaped release paper covering and adhered to the adhesive regions on the membrane.
Figure 9:
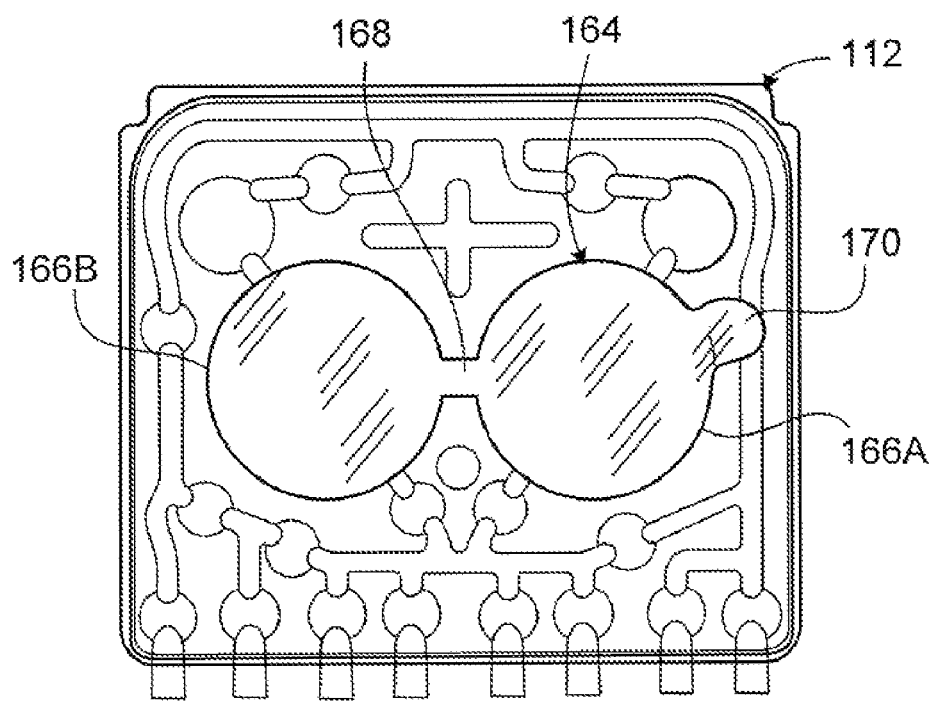
FIG. 9 is a plan view from the membrane side of the PD cassette of the PD system of FIG. 1 with eyeglass-shaped release paper covering and adhered to the adhesive regions on the membrane.

As shown in FIGS. 8 and 9, when initially provided to the user, the cassette 112 includes a generally eyeglass-shaped release paper 164 (e.g., wax-coated paper) that covers the adhesive 161 overlying the pump chambers 138A, 138B. Such a release paper can, for example, prevent debris and contaminants from collecting on the adhesive 161 during storage and handling of the cassette 112. The release paper 164 can be peeled off of the cassette 112 to expose the adhesive 161 prior to loading the cassette 112 into the cassette enclosure 114 of the PD cycler 102.

The release paper 164 includes two circular portions 166A, 166B and a connector portion 168 that extends between the two circular portions 166A, 166B. The circular portions 166A, 166B cover the adhesive laden regions 162A, 162B of the cassette membrane 140. The release paper 164 also includes a pull tab 170 that extends beyond the outer boundary of the adhesive 161 such that the pull tab 170 is not attached to the adhesive 161. A user can remove the release paper 164 to expose the adhesive 161 by pulling the pull tab 170. As the pull tab 170 is pulled away from the cassette 112, the connector portion 168 of the release paper 164 facilitates removal of both circular portions 166A, 166B of the release paper 164 through a single, continuous motion.

Figure 10:
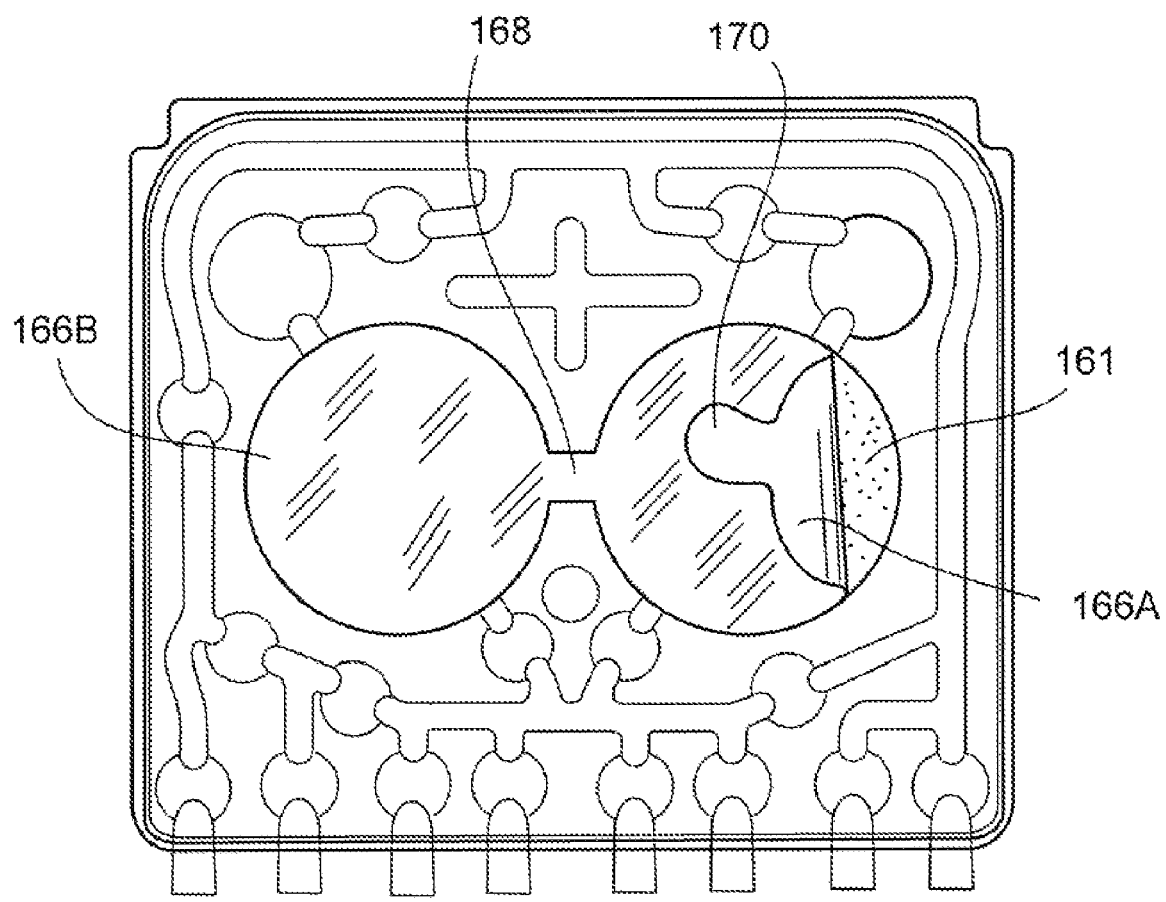
FIG. 10 is a plan view of the PD cassette of FIGS. 8 and 9 showing the eyeglass-shaped release paper being removed from the adhesive regions on the membrane.

Referring to FIG. 10, to prepare the PD cassette 112 for use, the release paper 164 is first peeled away from the membrane 140 of the cassette 112 by grasping and pulling the pull tab 170. This exposes the adhesive 161 initially positioned beneath the release paper 164. The release paper 164 can be discarded after removing it from the cassette 112.

Figure 11:
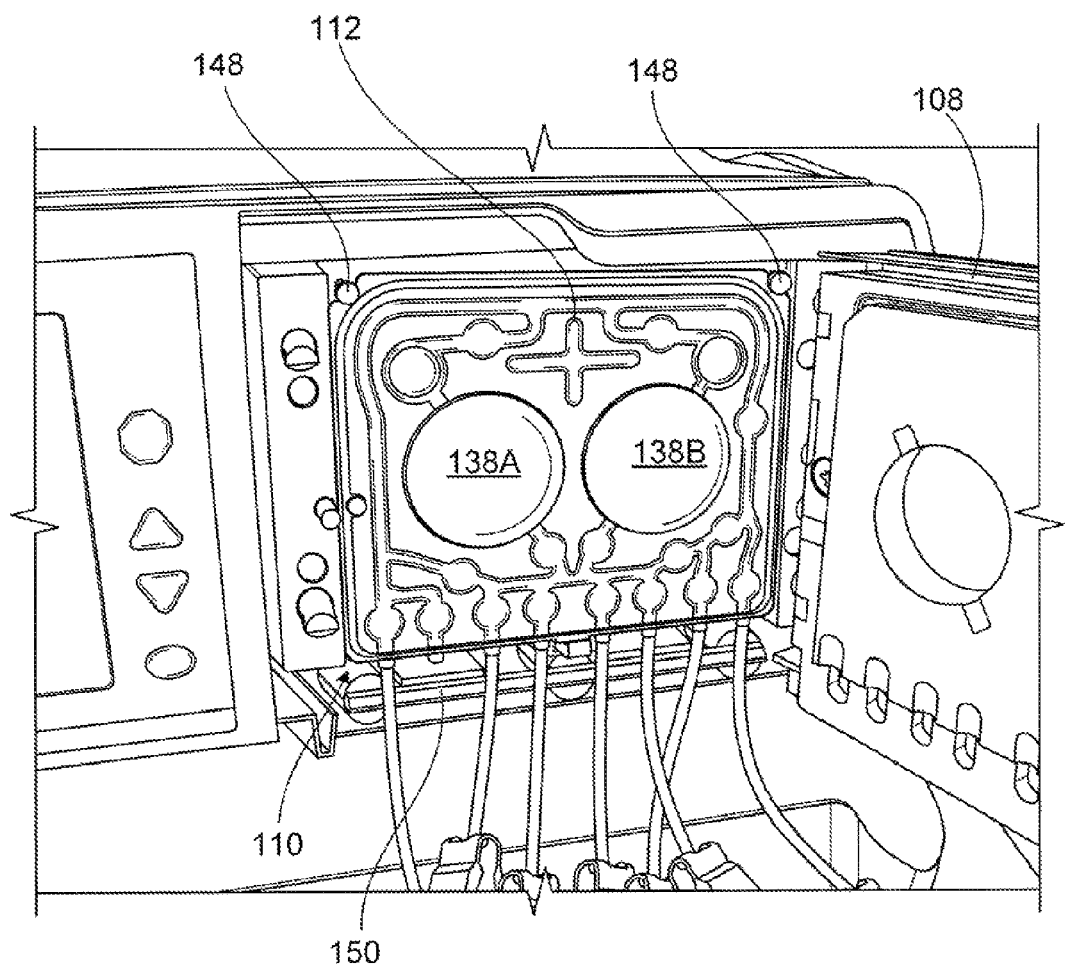
FIG. 11 is a partial perspective view of the PD cassette in the cassette compartment of the PD cycler of the PD system of FIG. 1.

As shown in FIG. 11, the door 108 of the PD cycler 102 is then opened to expose the cassette interface 110, and the cassette 112 is positioned adjacent to the interface 110 such that the adhesive 161 on the regions 162A, 162B of the membrane 140 overlying the pump chambers 138A, 138B of the cassette 112 is facing and is aligned with the piston heads 134A, 134B. In order to ensure that the adhesive 161 aligns with the piston heads 134A, 134B, the cassette 112 is positioned between the locating pins 148 and the lower ledge 150 extending from the cassette interface 110. The asymmetrical positioning of the connectors 160 of the cassette act as a keying feature that reduces the likelihood that the cassette 112 will be installed with the adhesive facing in the wrong direction (e.g., facing outward toward the door 108). Additionally or alternatively, the locating pins 148 can be dimensioned to be less than the maximum protrusion of the hemispherical projections 154A, 154B such that the cassette 112 cannot contact the locating pins 148 if the adhesive covered regions 162A, 162B of the membrane 140 are facing outward toward the door 108.

While loading the cassette 112 into the PD cycler 102, the piston heads 134A, 134B are completely retracted within the piston access ports 136A, 136B. This positioning of the piston heads 134A, 134B can reduce the likelihood of damage to the piston heads 134A, 134B during installation of the cassette 112. This positioning of the piston heads 134A, 134B can also facilitate positioning the cassette 112 against the cassette interface 110 before closing the door 108. For example, this positioning can help to ensure that the adhesive 161 is not inadvertently attached to the piston heads 134A, 134B prior to properly positioning the cassette 112 within the cassette enclosure 114.

Figure 12A:
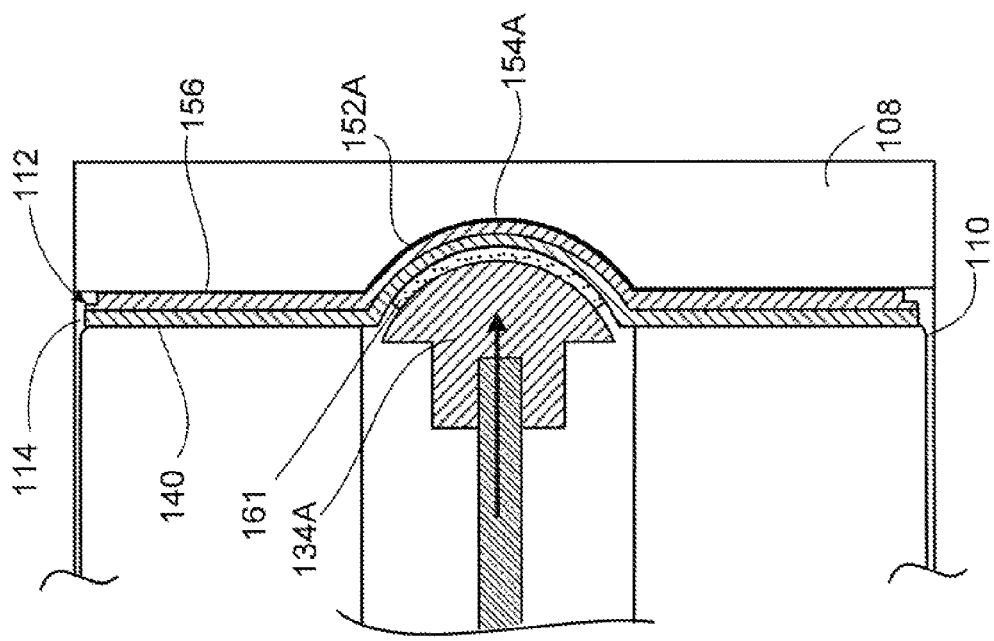
FIGS. 12A-12C are diagrammatic cross-sectional views of the PD cassette in the cassette compartment of the PD cycler of the PD system of FIG. 1, during different phases of operation.

Referring to FIG. 12A, with the cassette 112 positioned adjacent to the cassette interface 110, the door 108 is closed over the cassette 112 such that the cassette 112 is substantially contained within the cassette enclosure 114 between the door 108 and the cassette interface 110. As shown, the hemispherical projections 154A, 154B of the cassette 112 fit within the recesses 152A, 152B in the door 108. Because the PD system 100 does not require a vacuum system to move the portions 162A, 162B of the membrane 140 overlying the pump chambers 138A, 138B, a substantially airtight seal between the door 108 and the cassette interface 110 is typically not required. Thus, as compared to systems including a vacuum system adapted to retract portions of the cassette membrane overlying pump chambers, the door sealing mechanism of the PD cycler 102 can be simpler and more cost effective.

Figure 12B:
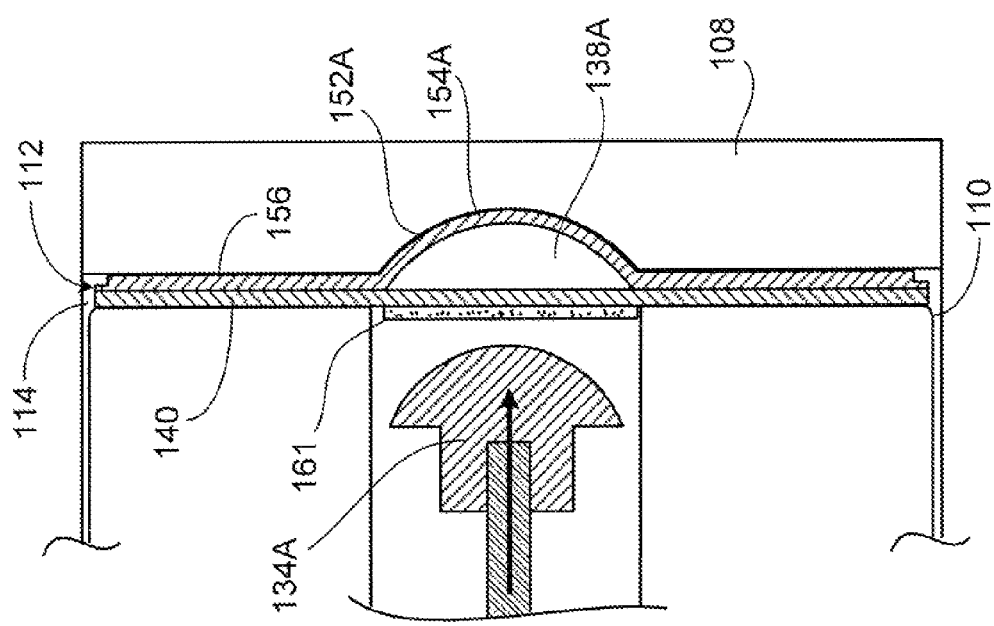

As shown in FIG. 12B, with the cassette 112 secured within the enclosure 114, the piston heads 134A, 134B are moved outward (e.g., to a substantially fully extended position) to contact the adhesive 161 disposed on the regions 162B, 162B of the cassette membrane 140. In this fully extended position, the inner surface of the membrane 140 comes into contact or near contact with the inner surface of the hemispherical projections 154A, 154B of the rigid base 156 of the cassette 112. The contact between the piston heads 134A, 134B and the adhesive 161 causes the adhesive 161 to adhere to the piston heads 134A, 134B. Because the adhesive 161 is also adhered to the membrane 140 of the cassette 112, the adhesive 161 secures the piston heads 134A, 134B to the membrane 140.

Figure 12C:
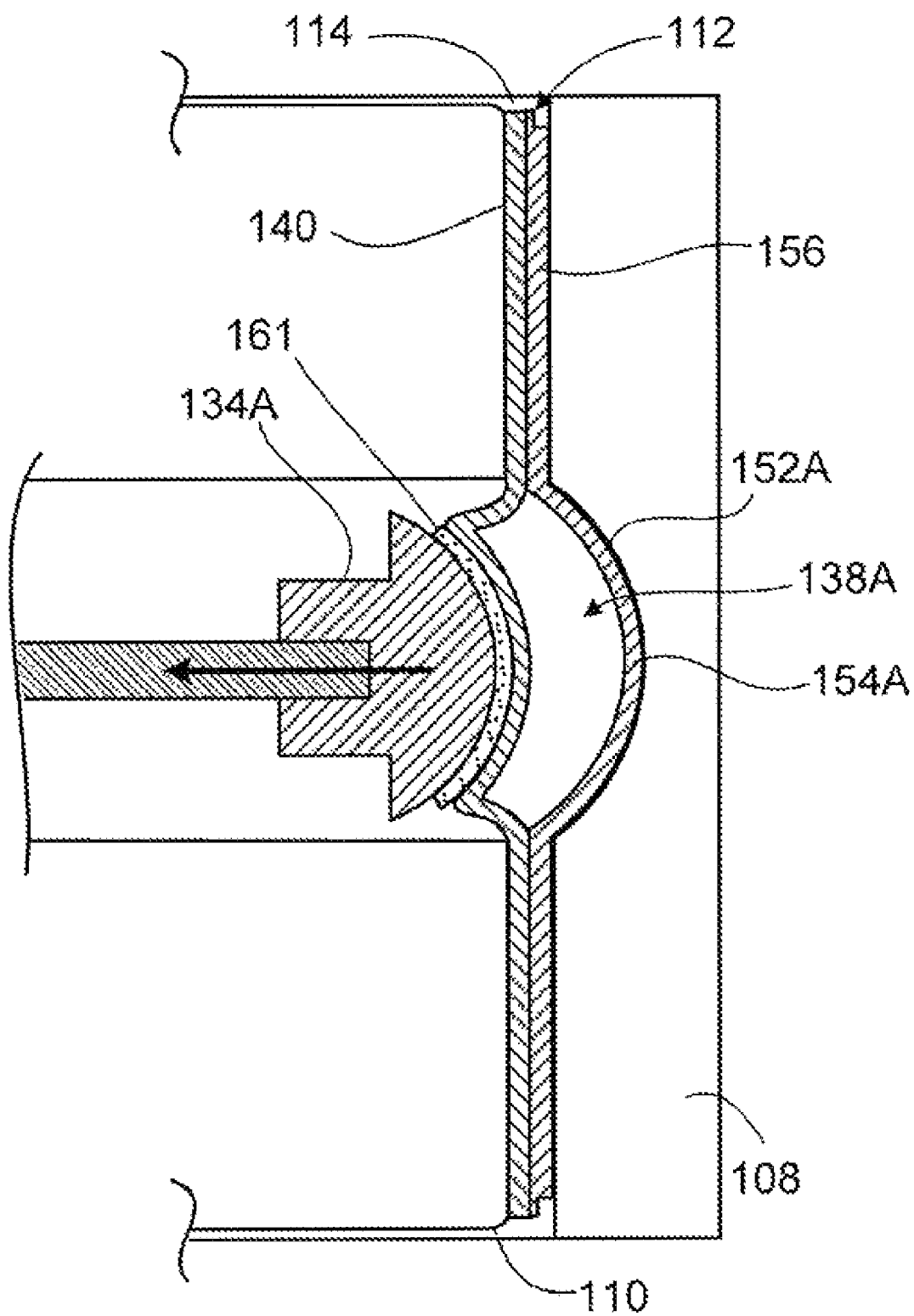

With the piston heads 134A, 134B adhesively attached to the membrane 140, PD solution can be drawn into the pump chambers 138A, 138B of the cassette 112 by retracting the membrane 140 along with the piston heads 134A, 134B to increase the volume of the pump chambers 138A, 138B, as shown in FIG. 12C. The fluid can then be forced out of the pump chambers 138A, 138B by again returning the piston heads 134A, 134B to the position shown in FIG. 12B, causing the membrane 140 to move toward the rigid base 156 and thus decreasing the volume of the pump chambers 138A, 138B. As noted above, while forcing PD solution into and out of the pump chambers 138A, 138B, certain inflatable members 142 of the PD cycler 102 can be selectively inflated to direct the pumped PD solution along desired pathways in the cassette 112.

Figure 13A:
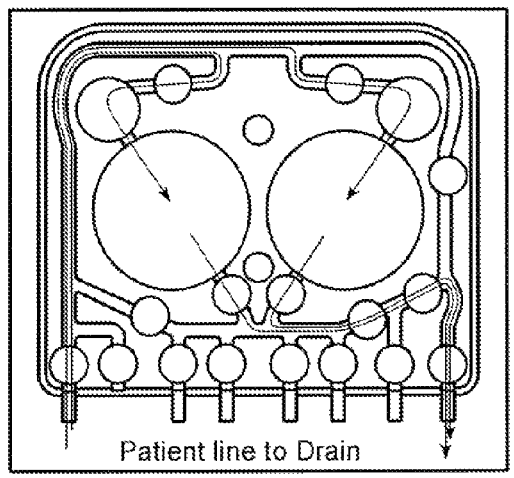
FIGS. 13A-13C illustrate various fluid flow paths through the PD cassette of the PD system of FIG. 1 during a PD treatment.

Referring back to FIGS. 1 and 2, during PD treatment, the patient line 130 is connected to a patient's abdomen via a catheter, and the drain line 132 is connected to a drain or drain receptacle. The PD treatment typically begins by emptying the patient of spent PD solution that remains in the patient's abdomen from the previous treatment. To do this, the pump of the PD cycler 102 is activated to cause the piston heads 134A, 134B to reciprocate and selected inflatable members 142 are inflated to cause the spent PD solution to be drawn into the pump chambers 138A, 138B of the cassette 112 from the patient and then pumped from the pump chambers 138A, 138B to the drain via the drain line 132. This flow path of the spent PD solution through the fluid pathways 158 in the cassette 112 is shown in FIG. 13A.

Figure 13B:
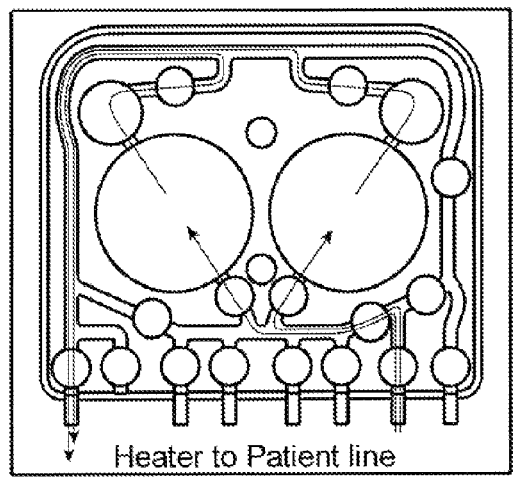

After draining the spent PD solution from the patient, heated PD solution is transferred from the heater bag 124 to the patient. To do this, the pump of the PD cycler 102 is activated to cause the piston heads 134A, 134B to reciprocate and certain inflatable members 142 of the PD cycler 102 are inflated to cause the spent PD solution to be drawn into the pump chambers 138A, 138B of the cassette 112 from the heater bag 124 via the heater bag line 128 and then pumped from the pump chambers 138A, 138B to the patient via the patient line 130. This flow path of the PD solution through the fluid pathways 158 in the cassette 112 is shown in FIG. 13B.

Figure 13C:
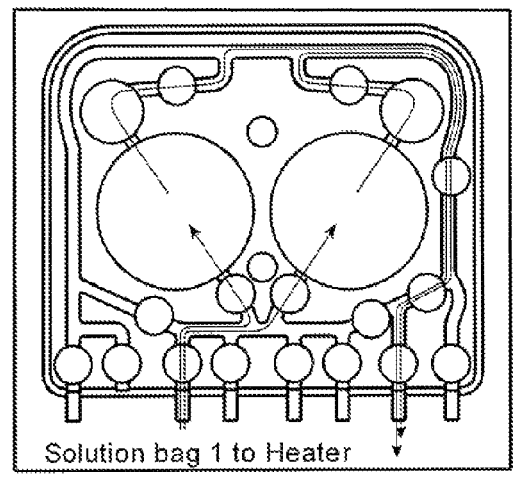

Once the PD solution has been pumped from the heater bag 124 to the patient, the PD solution is allowed to dwell within the patient for a period of time. During this dwell period, toxins cross the peritoneum into the PD solution from the patient's blood. As the PD solution dwells within the patient, the PD cycler 102 prepares fresh dialysate for delivery to the patient in a subsequent cycle. In particular, the PD cycler 102 pumps fresh PD solution from one of the four full PD solution bags 122 into the heater bag 124 for heating. To do this, the pump of the PD cycler 102 is activated to cause the piston heads 134A, 134B to reciprocate and certain inflatable members 142 of the PD cycler 102 are inflated to cause the PD solution to be drawn into the pump chambers 138A, 138B of the cassette 112 from the selected PD solution bag 122 via its associated line 126 and then pumped from the pump chambers 138A, 138B to the heater bag 124 via the heater bag line 128. This flow path of the PD solution through the fluid pathways 158 in the cassette 112 is shown in FIG. 13C.

After the PD solution has dwelled within the patient for the desired period of time, the spent PD solution is pumped from the patient to the drain. The heated PD solution is then pumped from the heater bag 124 to the patient where it dwells for a desired period of time. These steps are repeated with the PD solution from two of the three remaining PD solution bags 122. The PD solution from the last PD solution bag 122 is typically delivered to the patient and left in the patient until the subsequent PD treatment.

The PD cycler is typically used in an alternating pumping mode in which one piston head is protracted while the other piston head is retracted. Thus, as fluid drawn into one pumping chamber, fluid is simultaneously expelled from the other pumping chamber.

The adhesive attachment between the piston heads 134A, 134B and the membrane 140 can result in a substantially direct correlation between the position of the piston heads 134A, 134B and the volume of fluid drawn into and pumped out of the pump chambers 138A, 138B of the cassette 112. Such a direct correlation can improve the speed and accuracy of volumetric calculations of PD solution drawn into and pumped out of the cassette 112.

After completion of the PD treatment, the piston heads 134A, 134B are retracted away from the cassette 112 (e.g., perpendicular to the cassette 112) to a distance sufficient to allow the adhesive 161 to detach from the piston heads 134A, 134B and with a force that exceeds the adhesion strength or affinity of the adhesive 161 to the piston heads 134A, 134B. With this motion, the piston heads 134A, 134B become completely detached from the adhesive 161. Because the adhesion strength or affinity of the adhesive 161 to the membrane 140 is greater than the adhesion strength or affinity of the adhesive 161 to the piston heads 134A, 134B, the adhesive 161 remains adhered to the cassette 112 after the piston heads 134A, 134B have been detached. This helps to reduce or eliminate adhesive build-up on the piston heads 134A, 134B through repeated use. With the piston heads 134A, 134B detached from the adhesive 161, the door 108 of the PD cycler 102 is opened to expose the cassette 112, and the cassette 112, including the adhesive thereon, is removed from the cassette enclosure 114 by moving the bottom portion of the cassette 112 away from the cassette interface 110 and disengaging the top portion of the cassette 112 from the locating pins 148. In some cases, the cassette 112 is then discarded along with the fluid lines attached to the cassette 112. Because the adhesive 161 detaches from the piston heads 134A, 134B, it will generally be unnecessary for the user to clean the piston heads 134A, 134B prior to a subsequent use with a new cassette.

Figure 14A:
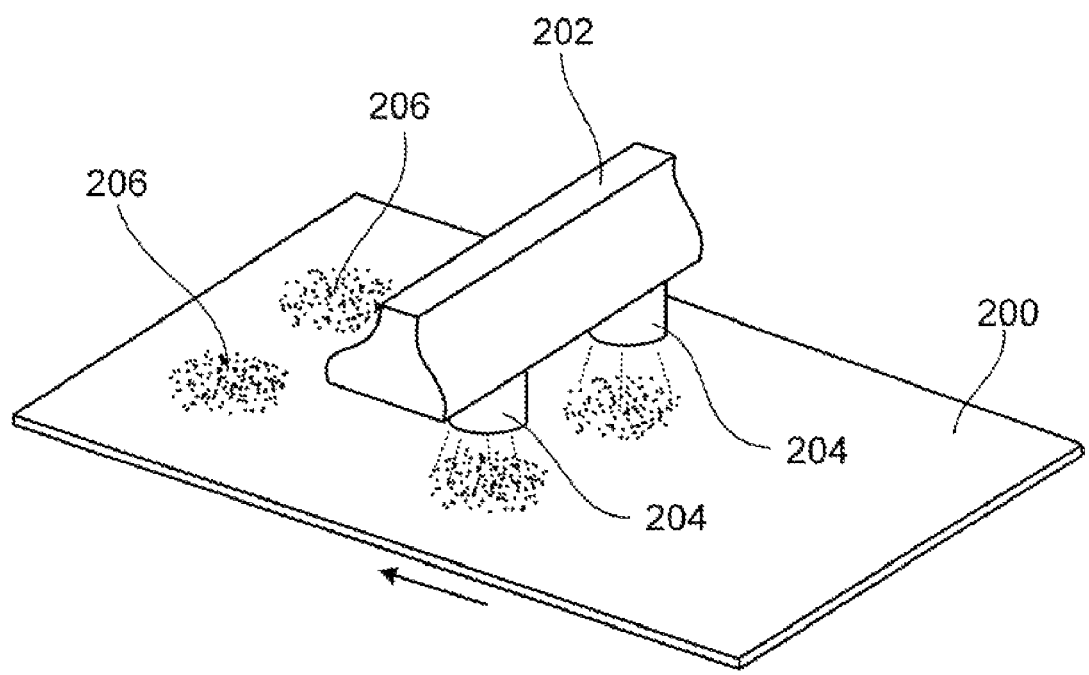
FIGS. 14A-14C illustrate a method of making eyeglass-shaped composites of adhesive regions disposed between and adhered to two release papers.
Figure 14B:
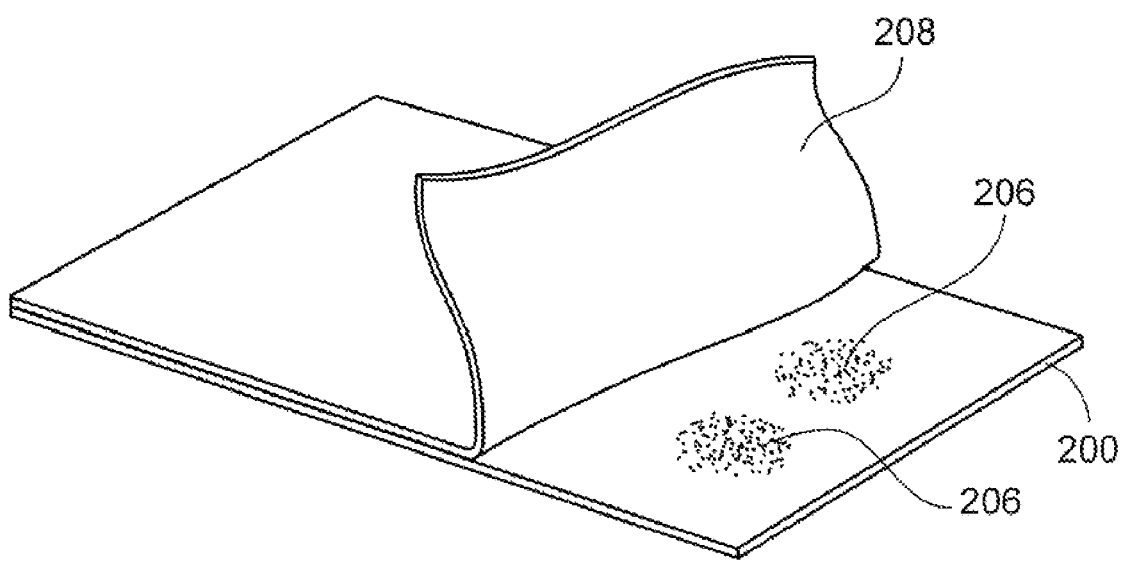
Figure 14C:
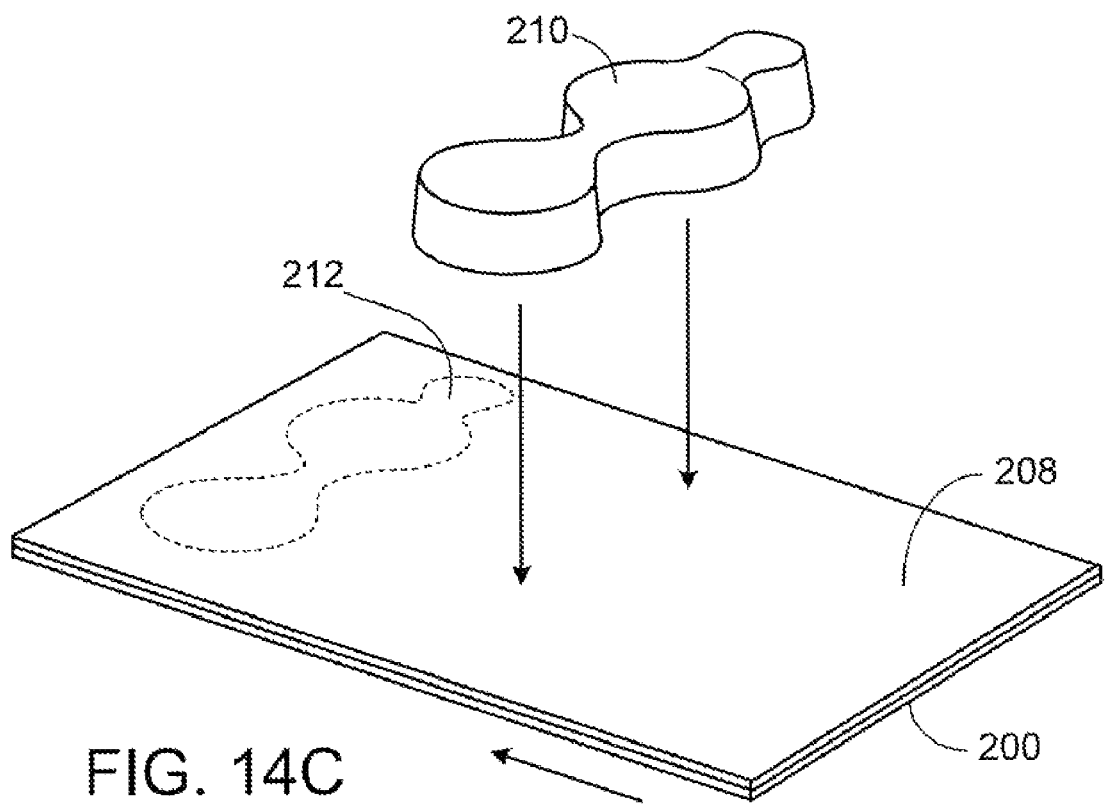

FIGS. 14A-14C illustrate a method of preparing eyeglass-shaped composites of adhesive and release paper that are used to apply the adhesive 161 and release paper 164 to the membrane 140 of the cassette 112. Referring to FIG. 14A, the adhesive 161 is first sprayed onto the top surface of a sheet of release paper (e.g., a sheet of wax-coated paper) 200 by a sprayer 202 including two spray nozzles 204. The adhesive 161 is sprayed onto the sheet of release paper 200 in pairs of circular adhesive regions 206 that are longitudinally spaced from each other along the sheet of release paper 200. The sprayer 202 is intermittently activated while the sheet of release paper 200 is continuously passed under the nozzles 204 to create the longitudinally spaced adhesive regions 206. The circular adhesive regions 206 within each pair are sized to correspond to the size of the pump chambers 138A, 138B of the cassette 112 (i.e., the largest diameter of the pump chambers 138A, 138B), and the circular adhesive regions 206 within each pair are laterally spaced from one another across the sheet of release paper 200 by substantially the same distance that the pump chambers 138A, 138B of the cassette 112 are laterally spaced from one another. As an alternative to using two separate nozzles configured to create the circular adhesive regions, a large surface area sprayer can be equipped with a stencil with circular shaped openings such that only adhesive passing though the openings will reach the sheet of release paper 200 while the remaining adhesive accumulates on the stencil. In addition, as an alternative to spraying the adhesive onto the sheet of release paper 200, any of various other techniques for applying the adhesive to the sheet of release paper 200 can be used. Examples of other techniques include dip coating, pouring, painting, etc.

As shown in FIG. 14B, after applying the adhesive circular regions to the top surface of the sheet of release paper 200, another sheet of release paper 208 is disposed over the circular adhesive regions 206 and secured to the first sheet of release paper 200 by the adhesive regions 206. The resulting composite sheet includes a discontinuous layer of circular adhesive regions 206 sandwiched between the two sheets of release paper 200, 208.

Referring to FIG. 14C, a generally eyeglass-shaped cutter 210 is then forced through the composite sheet at multiple, longitudinally spaced positions along the sheet to form multiple generally eyeglass-shaped composites. The cutter 210 includes a sharp cutting edge that extends around its periphery on its lower surface. The cutter 210 is manipulated to cut through the composite along a path that encompasses each of the pairs of adhesive regions 206. To do this, the composite sheet is passed under the cutter 210 until one of the pairs of adhesive regions 206 within the composite sheet lies directly beneath the cutter 210 with cutting edges of the cutter 210 surrounding the pair of adhesive regions 206. At this point, the movement of the composite sheet is paused, and the cutter 210 punches through the composite sheet to form an eyeglass-shaped composite. This process is repeated to produce multiple eyeglass-shaped composites. Each eyeglass-shaped composite includes two circular adhesive shaped regions 206 sandwiched between two eyeglass-shaped layers of release paper. Each of the two layers of release paper includes a pull tab 212 that extends beyond the adhesive regions 206 to facilitate removal of the release paper by a user.

Figure 15:
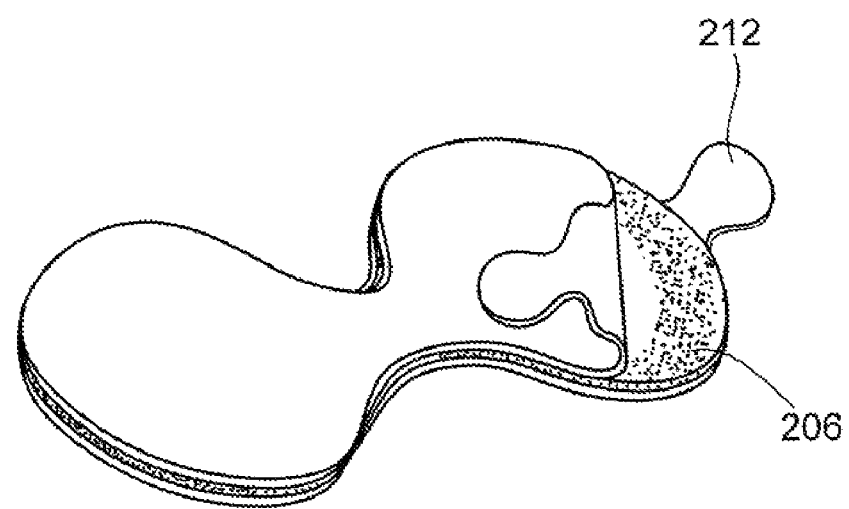
FIG. 15 is a perspective view of an eyeglass-shaped composite made using the method illustrated in FIGS. 14A-14C, showing one of the release papers of the composite being removed from the adhesive regions.

FIG. 15 shows one of the eyeglass-shaped composites produced from the above described method. As shown in FIG. 15, to permit the adhesive regions 206 to be secured to the regions 162A, 162B of the membrane 140 overlying the pump chambers 138A, 138B of the cassette 112, one of the release papers is peeled away from the adhesive by pulling on its pull tab 212.

Figure 16:
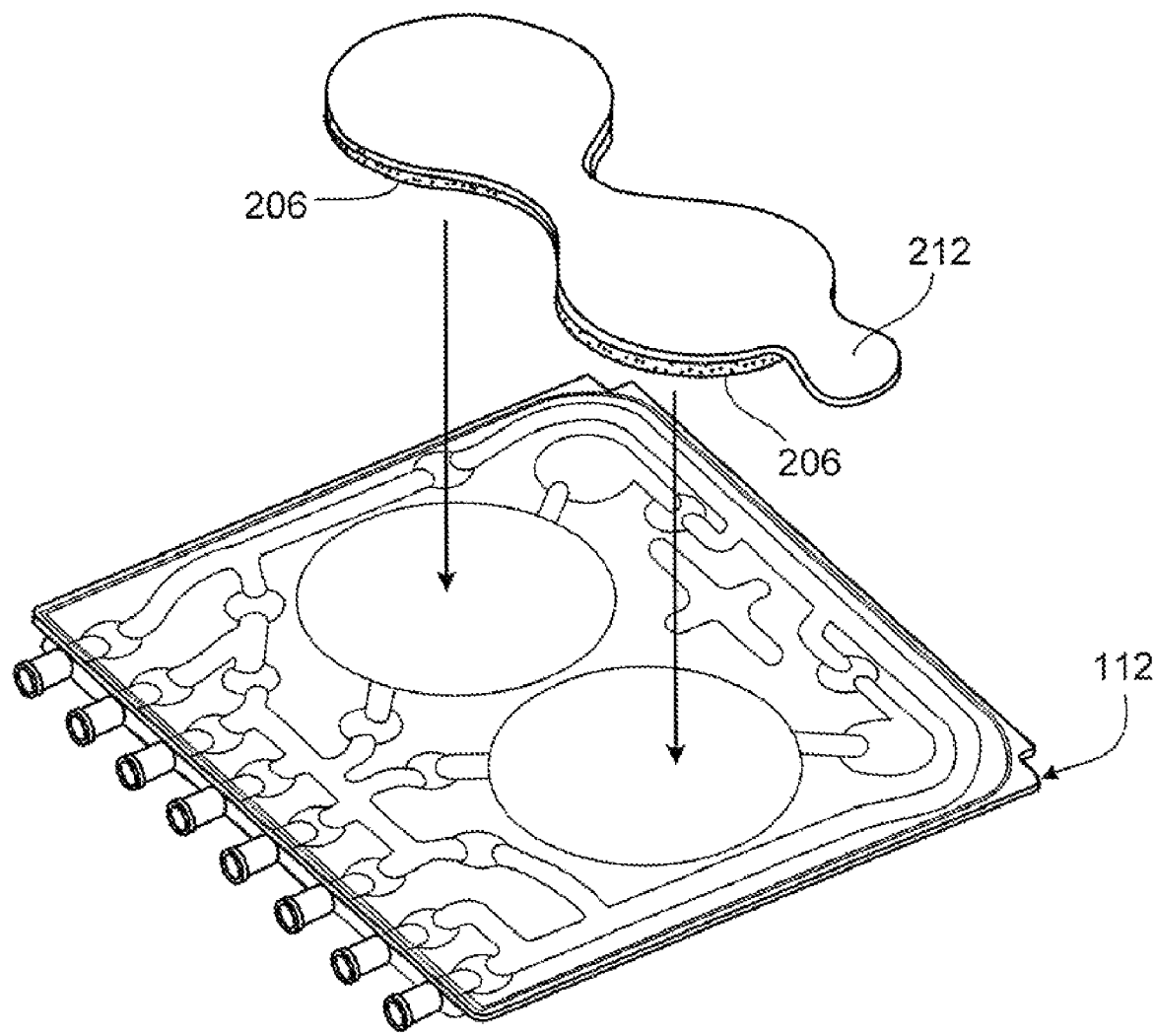
FIG. 16 is a perspective view of the eyeglass-shaped composite of FIG. 15 (with one of the release papers removed) being applied to the membrane of the PD cassette of the PD system of FIG. 1.

Referring to FIG. 16, the exposed adhesive regions are then applied to the portions 162A, 162B of the membrane 140 overlying the pump chambers 138A, 138B of the cassette 112. A set of fluid lines is then attached to the cassette, and the assembly of the cassette 112 and the attached fluid lines is packaged in a container (e.g., a bag and a box) for delivery to a user. At this point, the cassette 112, including the adhesive regions and release paper thereon, the fluid lines, and the packaging is sterilized with ethylene oxide (ETO). The release paper advantageously limits contact between the adhesive regions and the ETO during this sterilization process, which helps to maintain the integrity of the adhesive. Alternatively or additionally, the cassette 112 can be sterilized using other sterilization techniques, such as gamma or e-beam sterilization.

While certain implementations have been described, other implementations are possible.

Figure 17:
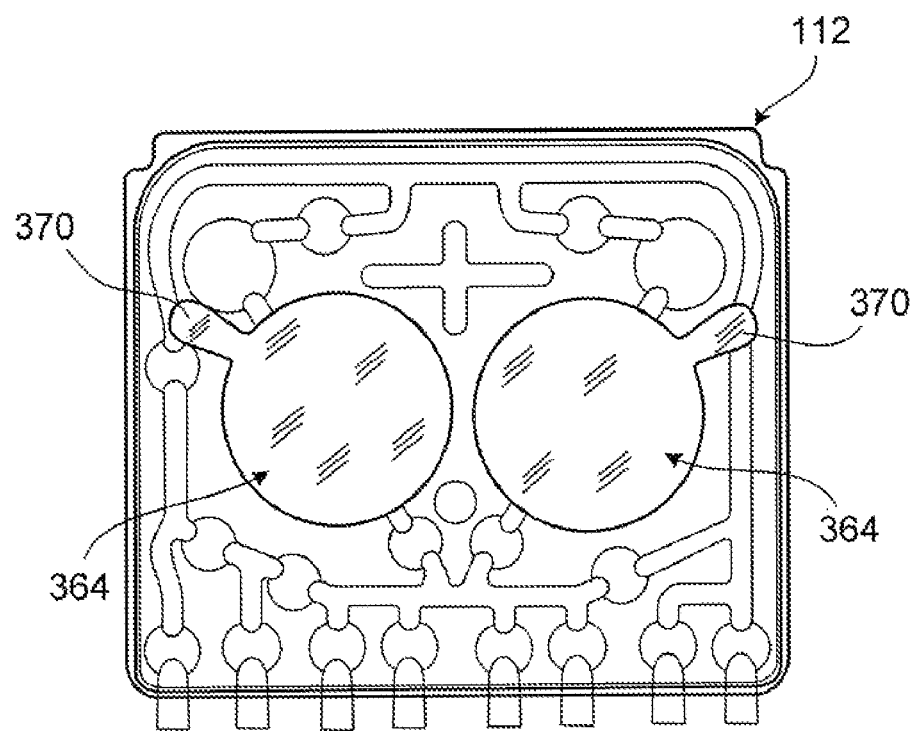
FIG. 17 is a plan view of a PD cassette with discrete release papers including pull tabs covering and adhered to the adhesive regions.

While the release paper 164 has been described as having a generally eyeglass shape, other types of release papers can be used. In some implementations, as shown in FIG. 17, for example, two substantially circular shaped release papers 364 are used to cover the adhesive regions. Each of the release papers 364 includes a pull tab 370 that extend beyond the outer boundary of the adhesive region to facilitate removal of the release paper 364 from the adhesive.

Figure 18:
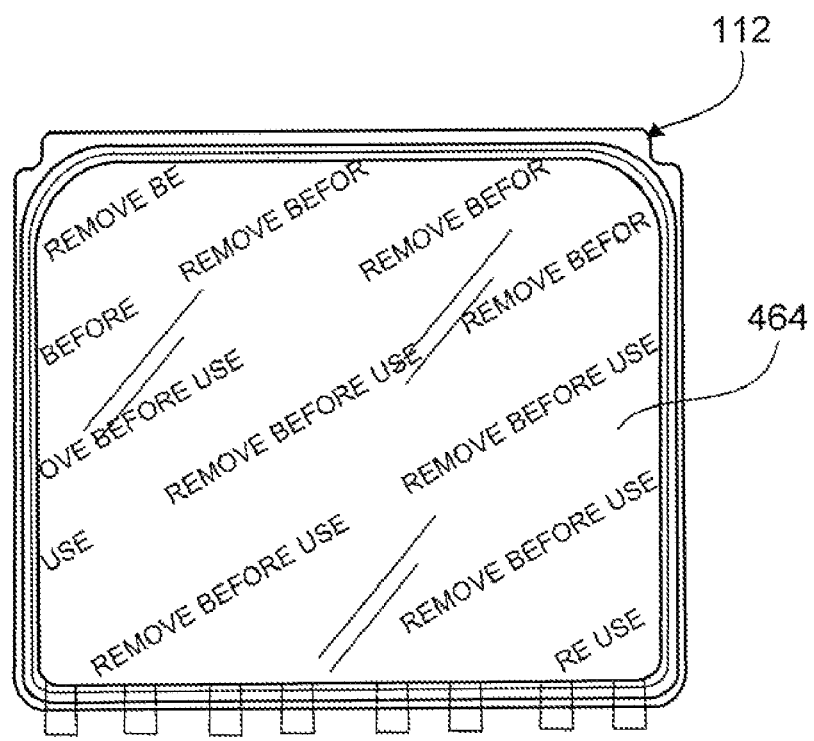
FIG. 18 is a plan view of a PD cassette with a release paper covering and adhered to the adhesive regions. The release paper is sized to cover substantially the entire surface of the cassette and includes printed text on its surface.

While the release papers described above are shaped to cover substantially only those regions of the cassette membrane 140 that include adhesive thereon, the release paper can be dimensioned to cover any of various different areas of the cassette membrane 140. In some implementations, as shown in FIG. 18, for example, a release paper 464 covers substantially the entire membrane 140 of the cassette 112. This can help protect the cassette membrane 140 from damage and/or contamination prior to use. One of the corners of the release paper 464 can be used as a pull tab to facilitate removal of the release paper 464 from the adhesive. As shown, the release paper 464 bears printed text that reminds the user to remove the release paper 464 before use. Any of the various other release papers described herein could include similar text.

While the adhesive 161 has been described as being initially disposed on the membrane 140 of the cassette 112, other arrangements are possible. In some implementations, for example, the adhesive 161 is initially disposed on the piston heads 134A, 134B. In certain implementations, the adhesive 161 remains on the piston heads 134A, 134B after the cassette 112 has been removed from the cassette enclosure 114 of the PD cycler 102. For example, the adhesive 161, the membrane 140 of the cassette 112, and the piston heads 134A, 134B can be formed of materials such that the adhesive 161 has a greater adhesion or affinity with the piston heads 134A, 134B than with the membrane 140. Because the adhesive 161 remains on the piston heads 134A, 134B, the adhesive 161 can be reused through multiple PD treatments, or the user can remove the adhesive 161 from the piston heads 134A, 134B between treatments. In other implementations, the materials of the adhesive 161, the membrane 140 of the cassette 112, and the piston heads 134A, 134B can be selected such that the adhesive 161 has a greater adhesion or affinity with the membrane 140 than with the piston heads 134A, 134B. In such cases, the adhesive 161 would ultimately remain adhered to the cassette 112 that is removed from the PD cycler 102 and discarded.

While the adhesive differential between the piston heads 134A, 134B and the membrane 140 has been described as being achieved through a combination of materials including forming the piston heads 134A, 134B of polyoxymethylene and the membrane 140 from the above-described multi-layer laminate while using a synthetic rubber adhesive, other material combinations that provide levels of adhesion between the adhesive and the piston heads and between the adhesive and the cassette membrane to allow the piston heads to retract the membrane during treatment and to allow the piston heads to be detached from the membrane after treatment without detaching the adhesive from the cassette membrane can be used.

In certain implementations, for example, the adhesive can be formed of any of various other types of materials that have adhesion properties similar to the synthetic rubber adhesive described above. For example, the adhesive can be a natural rubber adhesive or an acrylic adhesive. The piston heads 134A, 134B can be formed of one or more polyvinyl chlorides (PVC), polyamides, polycarbonates, ethyl vinyl acetates, and/or polysulfones. The membrane 140 can be formed of any of various types of polyolefins (e.g., high density polyethylenes (HDPE), low density polyethylenes (LDPE), or combinations of HDPE and LDPE) and/or polyvinylchlorides (PVC).

In certain implementations, the adhesive 161 is formed of natural rubber adhesive, the piston heads 134A, 134B are formed of polyoxymethylene plastic, and the membrane 140 is formed of polyolefin. In other implementations, the adhesive 161 is formed of acrylic co polymer, the piston heads 134A, 134B are formed of polycarbonate, and the membrane 140 is formed of PVC.

While the membrane 140 of the cassette 112 has been described as including three layers, the membrane of the cassette can alternatively include fewer than three layers. For example, the membrane can include two layers or only a single layer. Alternatively, the membrane of the cassette can include more than three layers.

While the base 156 of the cassette 112 has been described as being formed of polypropylene, the base 156 can be formed of any of various different rigid materials that are capable of being securely attached (e.g., thermally bonded, adhesively bonded) to the cassette membrane 140. In some implementations, for example, the base 156 is formed of polyvinyl chloride, polycarbonate, polysulfone, or other medical grade plastic materials.

While the piston heads 134A, 134B have been described as being formed of a single material that has a desired affinity for the adhesive, other types of piston head constructions can be used. For example, in some implementations, the piston head includes a core on which an outer layer or coating is applied. In such implementations, the outer layer or coating can be formed of a material that has the desired affinity for the adhesive while the core of the piston head can be formed of a different material that does not have the desired affinity for the adhesive. The outer layer or coating can, for example, be formed of any of the materials described above with regard to piston heads 134, 134B, and the core can be formed of any of various other materials, including polymers, metals, and/or alloys.

While the adhesion or affinity differential between the piston heads 134A, 134B and the membrane 140 has been described as being achieved through material selection, other methods of achieving the adhesion differential can alternatively or additionally be used. For example, the piston heads 134A, 134B can be roughened (e.g., through etching, through roughness built into a mold) to increase the surface area of the piston heads 134A, 134B. As compared to piston heads having smooth surfaces, such an increase in surface area can increase the adhesion between the adhesive 161 and the piston heads 134A, 134B and thus increase the types of materials that can be used for the piston heads 134A, 134B.

While the adhesive has been described as being applied in circular regions to the sheet of release paper before cutting the release paper into a desired shape (e.g., a generally eyeglass shape), in certain implementations, the adhesive is applied to (e.g., extruded onto) the sheet of release paper in a continuous layer. In such implementations, the adhesive would extend across the entire surface of the release paper/adhesive composite that is ultimately produced. In some implementations, the adhesive is not applied to an edge region of the sheet of release paper such that pull tabs of the release paper/adhesive composite can be cut from the edge region to facilitate removal of the release paper from the adhesive.

In certain cases, ready-to-use adhesive/release paper composites can be purchased from a supplier. In such cases, the release paper on one side of the adhesive would be removed from the composite and the exposed adhesive (with the other release paper secured to its opposite side) would be attached to the cassette membrane.

Figure 19:
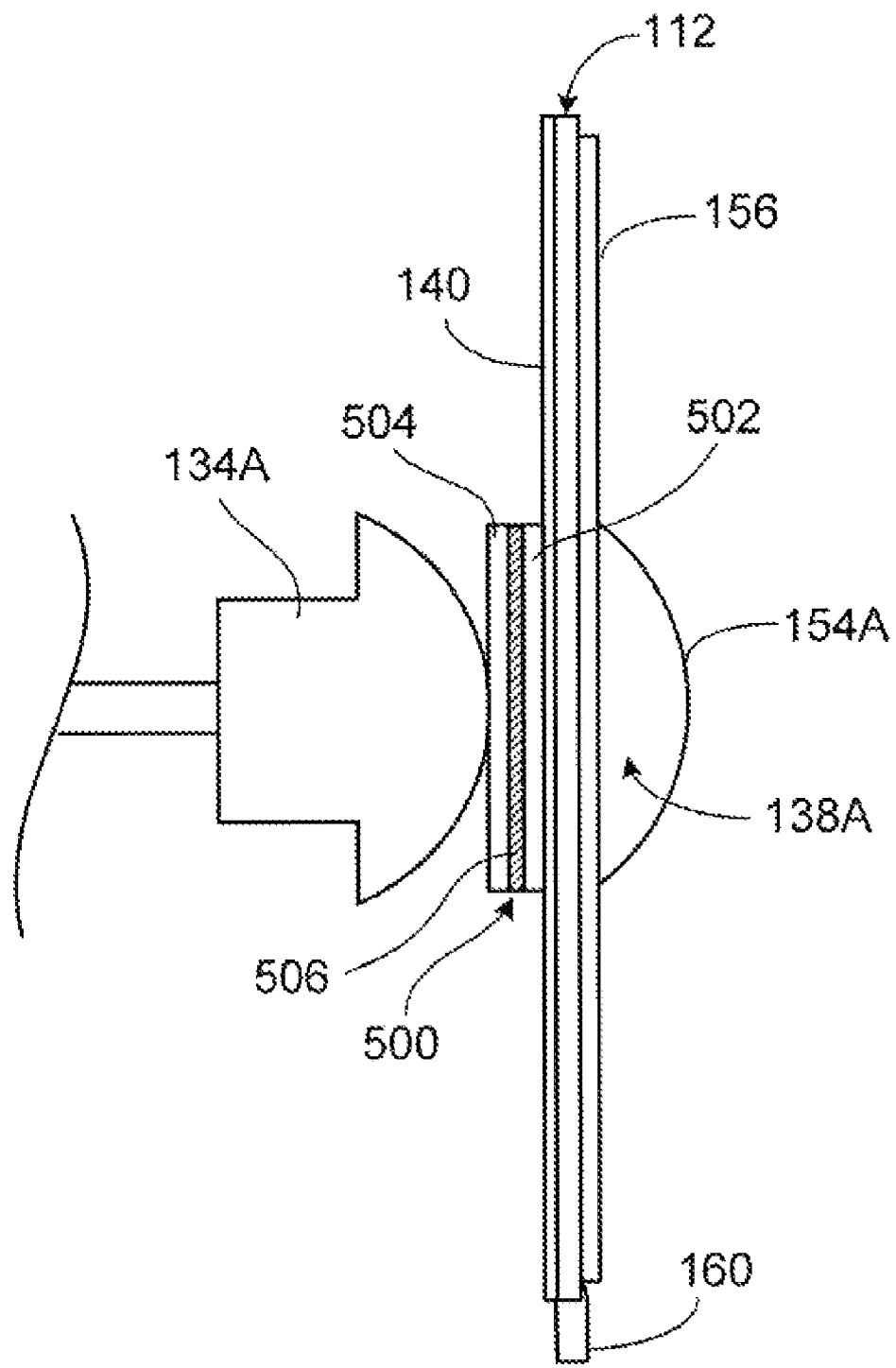
FIG. 19 is a side view of a piston head of the PD system of FIG. 1 and a PD cassette with a three-layer adhesive composite adhered to a membrane of the cassette.

In some implementations, multiple layers of adhesive are used to releasably attach the piston heads 134A, 134B to the membrane 140. For example, as shown in FIG. 19, a double-sided tape 500 is disposed between the piston heads 134A, 134B and the membrane 140. For improved clarity of the cassette, no components of the PD cycler 102 other than the piston head 134A and its related piston shaft, are shown in FIG. 19. The double-sided tape 500 includes a first adhesive layer 502 and a second adhesive layer 504 disposed on opposite sides of a base 506. The first adhesive layer 502 is affixed to portions 162A, 162B of the membrane 140 overlying the pump chambers 138A, 138B of the cassette 112. With the first adhesive layer 502 adhered to the membrane 140, the second adhesive layer 504 is exposed toward the piston heads 134A, 134B. During use, the piston heads 134A, 134B can be moved into contact with the second adhesive layer 504 to adhere the second adhesive layer 504 to the piston heads 134A, 134B. The first adhesive layer 502 in contact with the membrane 140 can be formed of a biocompatible adhesive to reduce the likelihood of contaminating the PD solution contained in the cassette 112. The second adhesive layer 504 in contact with the piston heads 134A, 134B can be formed of either a biocompatible or bioincompatible adhesive capable of achieving the desired adhesion to the material of the piston heads 134A, 134B. In implementations in which the first adhesive layer 502 is formed of a biocompatible adhesive and the second adhesive layer 504 is formed of a bioincompatible adhesive, the base 506 can be formed of low density polyethylene (LDPE). The LDPE base 506 can resist permeation of the bioincompatible adhesive of the second layer 504 and, thus, reduce the likelihood of contamination of the biocompatible adhesive in contact with the membrane 140.

The use of two or more different adhesives allows the cassette to be used with membrane/piston head material combinations different than those discussed above. For example, multiple different adhesive combinations can be used for different dialysis systems.

While double-sided tape 500 has been described as including a base 96, the two different adhesives can be directly adhered to one another, particularly if each adhesive is biocompatible.

While the adhesive has been described as being uniformly distributed across those regions 162A, 162B of the cassette membrane 140 that overlie the pump chambers 138A, 138B, other arrangements are possible. For example, in some implementations, the adhesive 161 is distributed over the regions 162A, 162B in a pattern.

While the piston heads 134A, 134B have been described as being axially moved to break the attachment between the adhesive and the piston heads 134A, 134B, other types of movements of the piston heads 134A, 134B can alternatively or additionally be used to break the attachment between the adhesive and the piston heads 134A, 134B. In some implementations, each piston head is at least partially rotatable about an axis perpendicular to a membrane to detach the piston head from the adhesive through a substantially shear force. In certain implementations, each piston head is moveable in a direction substantially parallel to the membrane to detach the piston head from the adhesive through a substantially shear force. By allowing the release of the piston head using a different type of force than the one used to move the membrane, the likelihood of inadvertent detachment of the piston head can be reduced.

While the piston heads 134A, 134B have been described as being moved (e.g., retracted, rotated, and/or laterally displaced) by a distance sufficient to completely detach the piston heads 134A, 134B from the adhesive, the piston heads 134A, 134B can alternatively be moved by a distance that causes the piston heads 134A, 134B to only partially detach from the adhesive. In such implementations, the user can complete the detachment of the piston heads 134A, 134B from the adhesive when the user pulls the cassette out of the cassette enclosure of the PD cycler.

While the adhesive has been described as being exposed through the removal of a release paper, other methods of exposing the adhesive are possible. For example, the adhesive can be formed on the cassette 112 through the chemical reaction of two materials on the cassette 112. In such a configuration, a first non-adhesive material can be initially disposed on regions 162A, 162B of the cassette 112, and a second material can be placed into contact with the first material to form an adhesive.

While the cassette 112 has been described as being positioned between the locating pins 148 and the lower ledge 150 extending from the cassette interface 110 in order to hold the cassette 112 in a position such that the piston heads 134A, 134B align with the pump chambers 138A, 138B, other techniques for ensuring that the piston heads 134A, 134B align with the pump chambers 138A, 138B can alternatively or additionally be used. In some implementations, for example, the cassette 112 is placed against the door 108 of the PD cycler 102 with the hemispherical projections 154A, 154B of the cassette 112 disposed in the recesses 152A, 152B of the door 108. The cassette 112 is held in this position by retainer clips attached to the door 108. Upon closing the door 108, the piston heads 134A, 134B of the PD cycler 102 align with the pump chambers 138A, 138B of the cassette 112. This technique helps to prevent the adhesive 161 from inadvertently sticking to the piston heads 134A, 134B or the cassette interface 110 when loading the cassette 112 into the PD cycler 102.

While the PD cycler 102 has been described as including a touch screen and associated buttons, the PD cycler can include other types of screens and user data entry systems. In certain implementations, for example, the cycler includes a display screen with buttons (e.g., feathertouch buttons) arranged on the console adjacent the display screen. Certain buttons can be arranged to be aligned with operational options displayed on the screen during use such that the user can select a desired operational option by pressing the button aligned with that operational option. Additional buttons in the form of arrow buttons can also be provided to allow the user to navigate through the various display screens and/or the various items displayed on a particular screen. Other buttons can be in the form of a numerical keypad to allow the user to input numerical values in order, for example, to input operational parameters. A select or enter button can also be provided to allow the user to select an operational option to which the user navigated by using the arrow keys and/or to allow the user to enter values that the user inputted using the numerical keypad.

While the adhesive laden cassettes described above have been described as being part of a PD system, these types of cassettes can be used in any of various other types of cassette-based medical fluid pumping systems, including hemodialysis systems.

What is claimed is:

1. A medical fluid pump system, comprising:
a movable piston head;
a cassette comprising
   a base defining an opening; and
   a membrane attached to the base covering the opening, the membrane together with the base defining a fluid pump chamber, a flow pathway that leads from the fluid pump chamber to an inlet of the cassette, and a flow pathway that leads from the fluid pump chamber to an outlet of the cassette, the cassette positioned so that the membrane faces the piston head and can be moved by the piston head to change a volume of the fluid pump chamber; and
an adhesive disposed between and in contact with the piston head and the membrane, wherein the adhesive has sufficient affinity for the piston head to allow the piston head to retract and deflect the membrane outward to increase the volume of the fluid pump chamber while maintaining adhesive contact with the membrane, and the adhesive has substantially greater affinity for the membrane than for the piston head such that the piston head can be retracted in a manner to separate the piston head from the adhesive without separating the adhesive from the membrane.

2. The medical fluid pump system of claim 1, wherein the piston head is adapted to be moved away from the cassette with a force sufficient to overcome the affinity between the piston head and the adhesive such that the piston head can be separated from the membrane.

3. The medical fluid pump system of claim 1, wherein the piston head is arranged to be moved a distance of at least 1.5 centimeters away from a plane in which the membrane lies when the membrane is not deformed by the piston head.

4. The medical fluid pump system of claim 1, wherein the system comprises a wall adjacent the cassette, and the piston head can be retracted beyond an outer surface of the wall.

5. The medical fluid pump system of claim 1, wherein the piston head comprises polyoxymethylene and the membrane comprises a low density polyolefin.

6. The medical fluid pump system of claim 5, wherein the adhesive comprises synthetic rubber.

7. The medical fluid pump system of claim 6, wherein the synthetic rubber is a double coated synthetic rubber tape.

8. The medical fluid pump system of claim 1, wherein an adhesion strength of the adhesive to the membrane is substantially greater than an adhesion strength of the adhesive to the piston head.

9. The medical fluid pump system of claim 1, wherein the adhesive comprises a first layer of adhesive in contact with the membrane and a second layer of adhesive in contact with the piston head.

10. The medical fluid pump system of claim 9, further comprising a base layer disposed between the first and second layers of adhesive.

11. The medical fluid pump system of claim 1, wherein the piston head is movable in a direction substantially perpendicular to the cassette.

12. The medical fluid pump system of claim 11, wherein the piston head can be separated from the adhesive by moving the piston head in the direction substantially perpendicular to the cassette.

13. The medical fluid pump system of claim 1, wherein the base of the cassette is a molded tray-like base.

14. The medical fluid pump system of claim 1, wherein the adhesive is disposed on a portion of the membrane overlying the fluid pump chamber.

15. The medical fluid pump system of claim 14, wherein the adhesive is substantially uniformly disposed on the portion of the membrane overlying the fluid pump chamber.

16. The medical fluid pump system of claim 1, wherein the medical system comprises first and second movable piston heads, and the membrane together with the base defines first and second fluid pump chambers, flow pathways that lead from the first and second fluid pump chambers to the inlet of the cassette, and flow pathways that lead from the first and second fluid pump chambers to the outlet of the cassette, and the cassette is positioned so that the membrane faces the first and second piston heads and can be moved by the first and second piston heads to alter volumes of the first and second fluid pump chambers, and adhesive is disposed between and in contact with the first and second piston heads and the membrane, and wherein the adhesive has sufficient affinity for the first and second piston heads to allow the first and second piston heads to retract and deflect the membrane outward to increase the volumes of the first and second fluid pump chambers while maintaining adhesive contact with the membrane, and the adhesive has substantially greater affinity for the membrane than for the first and second piston heads such that the first and second piston heads can be retracted in a manner to separate the first and second piston heads from the adhesive without separating the adhesive from the membrane.

17. The medical fluid pump system of claim 1, wherein the medical fluid pump system is a dialysis system.

18. The medical fluid pump system of claim 1, wherein the medical fluid pump system is a peritoneal dialysis system.

* * * * *